(12) United States Patent
Anunike

(10) Patent No.: US 12,150,881 B2
(45) Date of Patent: Nov. 26, 2024

(54) APPARATUS FOR PROTECTING FINGER, THUMB, AND HAND

(71) Applicant: Kenny Chidozie Anunike, Galena, OH (US)

(72) Inventor: Kenny Chidozie Anunike, Galena, OH (US)

(*) Notice: Subject to any disclaimer, the term of this patent is extended or adjusted under 35 U.S.C. 154(b) by 338 days.

(21) Appl. No.: 17/070,921

(22) Filed: Oct. 15, 2020

(65) Prior Publication Data

US 2021/0022899 A1 Jan. 28, 2021

Related U.S. Application Data

(63) Continuation-in-part of application No. 16/012,066, filed on Jun. 19, 2018, now Pat. No. 10,856,590.

(51) Int. Cl.
*A61F 5/01* (2006.01)
*A61H 1/02* (2006.01)

(52) U.S. Cl.
CPC ...... *A61F 5/013* (2013.01); *A61F 2005/0137* (2013.01); *A61F 2005/0141* (2013.01); *A61H 1/0288* (2013.01)

(58) Field of Classification Search
CPC .............. A61F 5/013; A61F 2005/0137; A61H 1/0288
See application file for complete search history.

(56) References Cited

U.S. PATENT DOCUMENTS

| | | | | |
|---|---|---|---|---|
| 852,972 | A * | 5/1907 | Mackay | A41D 19/015 2/21 |
| 1,268,103 | A * | 6/1918 | Fleming | A41D 13/087 2/21 |
| 1,951,190 | A * | 3/1934 | Gambee | D05B 91/04 2/21 |
| 4,677,971 | A * | 7/1987 | Lindemann | A61F 5/0118 473/62 |
| 4,766,612 | A * | 8/1988 | Patton, Sr. | A41D 19/01517 2/163 |
| 5,147,285 | A * | 9/1992 | Buxton | A61F 5/013 602/22 |
| 5,232,436 | A * | 8/1993 | Janevski | A61F 5/013 602/22 |
| 6,684,406 | B2 * | 2/2004 | Fowler | A41D 13/084 2/21 |
| 6,925,653 | B1 * | 8/2005 | King | A41D 13/087 2/21 |
| 7,402,148 | B2 * | 7/2008 | Brewer | A61F 5/013 602/20 |
| 8,028,347 | B2 * | 10/2011 | Chang | A63B 71/148 2/161.1 |

(Continued)

*Primary Examiner* — Alissa L Hoey

(57) ABSTRACT

A finger brace device is disclosed herein. The finger brace device can comprise a first hinge component configured to connect a proximal component configured to fit around at least a first portion of a finger near a wrist, to an intermediate component located at a central portion of the apparatus, wherein the proximal component is located at a lateral portion of the apparatus. Also disclosed is a second hinge component configured to connect the intermediate component of the apparatus to a distal component. Furthermore, a ball and socket joint is configured to allow a broad range of motion between the proximal component of the apparatus and the plate component.

20 Claims, 17 Drawing Sheets

(56) References Cited

U.S. PATENT DOCUMENTS

| | | | | |
|---|---|---|---|---|
| 8,262,594 | B2* | 9/2012 | Sandusky | A61F 5/0118 602/5 |
| 8,341,763 | B2* | 1/2013 | Geyer | A41D 19/01588 2/21 |
| 8,490,215 | B2* | 7/2013 | Mueller | A41D 19/01588 2/21 |
| 8,646,112 | B2* | 2/2014 | Nix | A63B 71/148 2/163 |
| 10,363,158 | B1* | 7/2019 | Rhinier | A61F 5/013 |
| 10,905,181 | B2* | 2/2021 | Rabbeth, Jr. | A61F 5/013 |
| 11,096,435 | B2* | 8/2021 | Kamphuis | A41D 19/01505 |
| 11,446,199 | B2* | 9/2022 | Hepp | A61F 5/0118 |
| 2005/0251078 | A1* | 11/2005 | Fleischmann | A41D 13/087 602/22 |
| 2006/0048259 | A1* | 3/2006 | Keppler | A41D 19/01588 2/21 |
| 2008/0196135 | A1* | 8/2008 | Gait | A41D 19/01588 2/21 |
| 2009/0172864 | A1* | 7/2009 | Fisher | A63B 71/148 2/163 |
| 2009/0222967 | A1* | 9/2009 | Winningham | A41D 13/05 2/21 |
| 2009/0307821 | A1* | 12/2009 | Chang | A41D 19/01588 2/21 |
| 2011/0035856 | A1* | 2/2011 | Power | A41D 13/087 2/21 |
| 2012/0144545 | A1* | 6/2012 | Lynn | A41D 13/087 2/21 |
| 2012/0304356 | A1* | 12/2012 | Brewer | A61F 5/013 2/16 |
| 2015/0094636 | A1* | 4/2015 | Miyazawa | A61F 5/013 602/22 |
| 2015/0189928 | A1* | 7/2015 | Wulf | A41D 13/087 2/16 |
| 2015/0366277 | A1* | 12/2015 | Rabbeth, Jr. | A63B 71/141 602/22 |
| 2018/0250153 | A1* | 9/2018 | Kleynhans | A61F 5/05875 |
| 2018/0317578 | A1* | 11/2018 | Furukawa | A41D 19/0058 |
| 2018/0368491 | A1* | 12/2018 | Anunike | A63B 71/14 |
| 2021/0267782 | A1* | 9/2021 | Kienzle | B33Y 80/00 |

* cited by examiner

1200

1210 — A PROXIMAL COMPONENT OF AN APPARATUS CAN BE CONNECTED TO A PROXIMAL COMPONENT OF A FINGER BRACE APPARATUS CONFIGURED TO FIT AROUND AT LEAST A FIRST PORTION OF A FINGER NEAR A WRIST, TO AN INTERMEDIATE COMPONENT LOCATED AT A CENTRAL PORTION OF THE FINGER BRACE APPARATUS, WHEREIN THE PROXIMAL COMPONENT IS LOCATED AT A LATERAL PORTION OF THE FINGER BRACE APPARATUS.

1220 — THE INTERMEDIATE COMPONENT CAN BE CONNECTED TO A DISTAL COMPONENT OF THE FINGER BRACE APPARATUS CONFIGURED TO FIT AROUND AT LEAST A SECOND PORTION OF THE FINGER NEAR A FINGERNAIL, WHEREIN THE DISTAL COMPONENT IS LOCATED AT A DISTAL PORTION OF THE APPARATUS.

1310 — A PROXIMAL COMPONENT OF AN APPARATUS CAN BE CONNECTED TO A PROXIMAL COMPONENT OF A FINGER BRACE APPARATUS CONFIGURED TO FIT AROUND AT LEAST A FIRST PORTION OF A FINGER NEAR A WRIST, TO AN INTERMEDIATE COMPONENT LOCATED AT A CENTRAL PORTION OF THE FINGER BRACE APPARATUS, WHEREIN THE PROXIMAL COMPONENT IS LOCATED AT A LATERAL PORTION OF THE FINGER BRACE APPARATUS.

1320 — THE INTERMEDIATE COMPONENT CAN BE CONNECTED TO A DISTAL COMPONENT OF THE FINGER BRACE APPARATUS CONFIGURED TO FIT AROUND AT LEAST A SECOND PORTION OF THE FINGER NEAR A FINGERNAIL, WHEREIN THE DISTAL COMPONENT IS LOCATED AT A DISTAL PORTION OF THE APPARATUS.

1330 — LOCKING THE FINGER BRACE APPARATUS USING A PLATE COMPONENT LOCATED ADJACENT TO A FIRST HINGE OF THE FINGER BRACE APPARATUS, TO PRECLUDE A BENDING OF THE FINGER BRACE APPARATUS BEYOND A TARGET ANGLE.

1410 — A PROXIMAL COMPONENT OF AN APPARATUS CAN BE CONNECTED TO A PROXIMAL COMPONENT OF A FINGER BRACE APPARATUS CONFIGURED TO FIT AROUND AT LEAST A FIRST PORTION OF A FINGER NEAR A WRIST, TO AN INTERMEDIATE COMPONENT LOCATED AT A CENTRAL PORTION OF THE FINGER BRACE APPARATUS, WHEREIN THE PROXIMAL COMPONENT IS LOCATED AT A LATERAL PORTION OF THE FINGER BRACE APPARATUS.

1420 — THE INTERMEDIATE COMPONENT CAN BE CONNECTED TO A DISTAL COMPONENT OF THE FINGER BRACE APPARATUS CONFIGURED TO FIT AROUND AT LEAST A SECOND PORTION OF THE FINGER NEAR A FINGERNAIL, WHEREIN THE DISTAL COMPONENT IS LOCATED AT A DISTAL PORTION OF THE APPARATUS.

1430 — LOCKING THE FINGER BRACE APPARATUS USING A PLATE COMPONENT LOCATED ADJACENT TO A FIRST HINGE OF THE FINGER BRACE APPARATUS, TO PRECLUDE A BENDING OF THE FINGER BRACE APPARATUS BEYOND A TARGET ANGLE.

1440 — CONNECTING THE FINGER BRACE APPARATUS WITH ANOTHER FINGER BRACE APPARATUS VIA A BAND.

FIG. 14

APPARATUS FOR PROTECTING FINGER, THUMB, AND HAND

CROSS-REFERENCE TO RELATED APPLICATION

This application claims priority to and claims the benefit of priority to U.S. Non-Provisional patent application Ser. No. 16/012,066, filed on Jun. 19, 2018 and titled "Apparatus for Protecting Finger, Hand, and Thumb" which claims priority to U.S. Provisional Patent Application No. 62/525,120, filed on Jun. 26, 2017 and entitled "Apparatus for Protecting Finger, Thumb, and Hand". The entirety of the disclosure of the aforementioned applications are considered part of, and is incorporated by reference in, the disclosure of this application.

TECHNICAL FIELD

This disclosure generally relates to finger brace devices and methods for protecting a finger and/or hand from injury.

BACKGROUND

Currently, participants of contact sports (e.g., football, soccer, basketball, etc.) or people belonging to professions that require the performance of strenuous activities, (e.g., law enforcement, construction, or military deployment), capable of potentially injuring the participant of such activities. In an instance, some of these injuries can occur to hands and/or fingers of the participants, such injuries including hyperextension and/or contusions of the fingers. In some instances, participants of such activities use gloves with padding materials and/or athletic tape to cover and protect the fingers and hand from high-impact injuries. Although gloves can protect the hand and fingers from contusions, the protective padding associated with the gloves are unable to prevent respective fingers from hyperextending and incurring torsion at the phalangeal joints. Also, many gloves attempting to protect fingers and/or hands from hyperextension requires the participant to sacrifice mobility and natural movement capabilities of the hand and fingers due to the bulkiness and fitting impediments associated with the glove with respect to the hand and fingers, in order to provide some protection against injuries.

Athletic tape is used as a means to tightly wrap fingers to secure movement, at the phalangeal joints, to the wrist and hand. This method allows for the fingers to remain in a fixed position to impede hyperextension, however, in some instances, athletic tape is made of materials that inadequately guard against high-impact forces thus allowing for a practitioner to still incur bruising and swelling to the fingers and hand. Similar to current protective gloves, using athletic tape to wrap and protect the fingers and hand does not allow for natural movement of the fingers and hand. Furthermore, the process of taping a hand and fingers requires much time, burden, and effort prior to performing a potentially injurious activity. Furthermore, in an aspect, applying athletic tape to hand and fingers is not as intuitive as sliding protective gloves onto a hand, since each finger must be wrapped in a unique manner to provide adequate protection from injury. As such, there are numerous problems and inefficiencies associated with existing mechanisms to protect a hand and fingers from injury Thus, new devices, systems, and methods are required to overcome such issues related to the protection of hands and/or fingers.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, systems, devices, apparatuses, and/or computer-implemented methods that facilitate the protection of fingers against hyperextension and other injuries are provided herein.

According to one embodiment, an apparatus is disclosed comprising a first hinge component configured to connect a proximal component configured to fit around at least a first portion of a finger near a wrist, to an intermediate component located at a central portion of the apparatus, wherein the proximal component is located at a lateral portion of the apparatus. In an aspect, the apparatus can further comprise a second hinge component configured to connect the intermediate component of the apparatus to a distal component configured to fit around at least a second portion of the finger near a fingernail, wherein the distal component is located at a distal portion of the apparatus.

According to another embodiment, a method is disclosed comprising connecting a proximal component of a finger brace apparatus, configured to fit around at least a first portion of a finger near a wrist, to an intermediate component located at a central portion of the finger brace apparatus, wherein the proximal component is located at a lateral portion of the finger brace apparatus. In another aspect, the method can further comprise connecting the intermediate component to a distal component of the finger brace apparatus configured to fit around at least a second portion of the finger near a fingernail, wherein the distal component is located at a distal portion of the apparatus.

The following description and the annexed drawings set forth in detail certain illustrative aspects of this disclosure. These aspects are indicative, however, of but a few of the various ways in which the principles of this disclosure may be employed. This disclosure intended to include all such aspects and their equivalents. Other advantages and distinctive features of this disclosure will become apparent from the following detailed description of this disclosure when considered in conjunction with the drawings.

DESCRIPTION OF THE DRAWINGS

Numerous aspects, embodiments, objects and advantages of the present invention will be apparent upon consideration of the following detailed description, taken in conjunction with the accompanying drawings, in which like reference characters refer to like parts throughout, and in which:

FIG. 12 illustrates a flow diagram of an example, non-limiting method of facilitating an assembly of an example apparatus.

FIG. 13 illustrates a flow diagram of an example, non-limiting method of facilitating an assembly of an example apparatus.

FIG. 14 illustrates a flow diagram of an example, non-limiting method of facilitating an assembly of an example apparatus.

DETAILED DESCRIPTION

Figure 1:
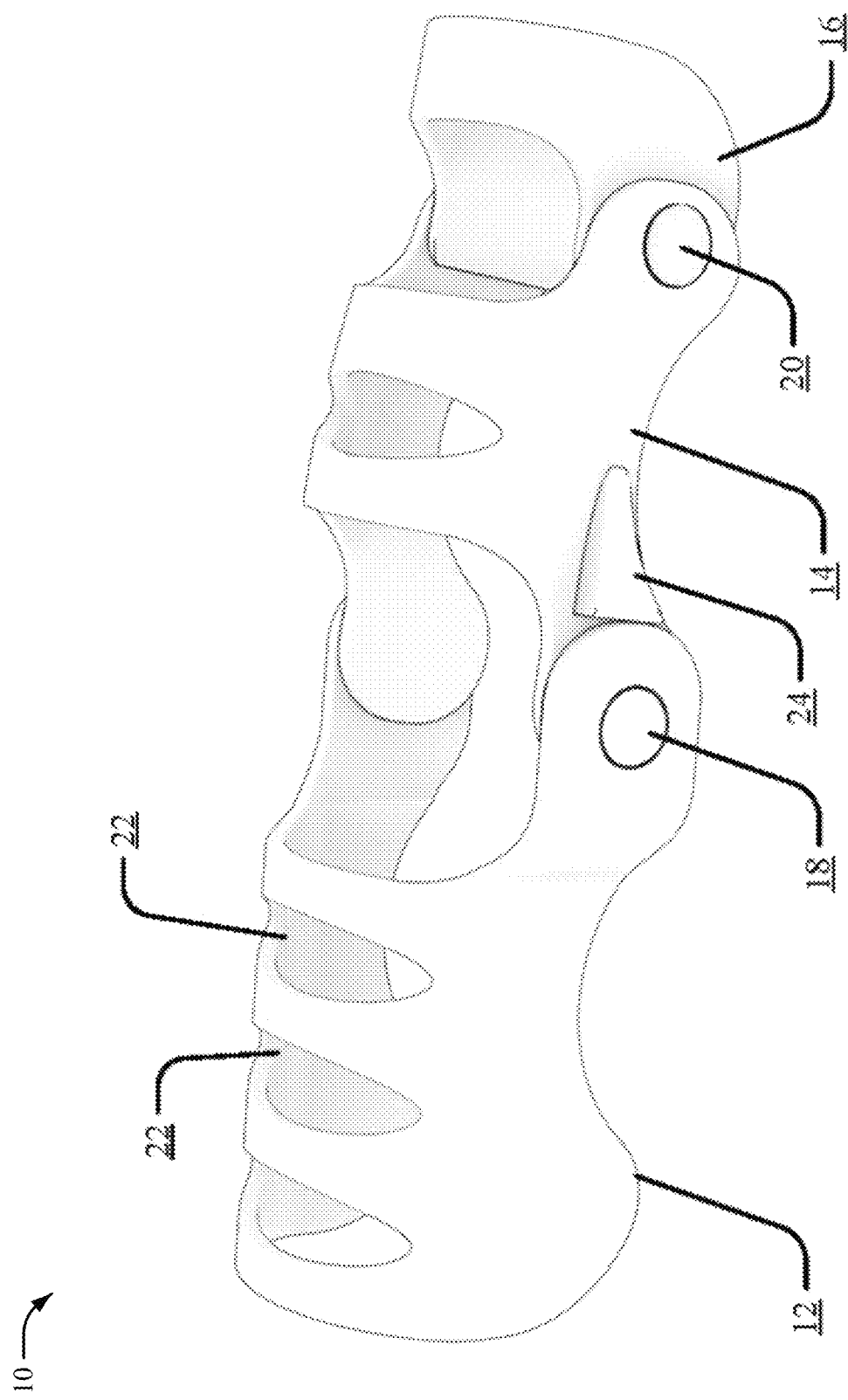
FIG. 1 illustrates a non-limiting high-level diagram of a perspective view of a non-limiting example apparatus configured to protect a finger and/or thumb, wherein the apparatus is positioned in a first position in accordance with one or more embodiments described herein.

The innovation is described with reference to the drawings, wherein like reference numerals are used to refer to like elements throughout. In the following description, for purposes of explanation, numerous specific details are set forth in order to provide a thorough understanding of this innovation. It may be evident, however, that the innovation can be practiced without these specific details. In other instances, well-known structures and components are shown in block diagram form in order to facilitate describing the innovation.

The subject disclosure is directed to a protective gear apparatus. Protective gear is described herein with reference to a "finger guard".

As used herein, the term "finger guard" means an apparatus for protecting a finger or a thumb of a hand to help protect the finger or thumb against injury and, in particular, impact and hyperextension injuries of the finger and thumb.

As used herein, the term "clothing" defines any article which is fitted over or attached to a portion of a body including appendages of the body, including protective gear and sports equipment.

As used herein, the term "proximal" when used to describe the finger guard defines an end of the finger guard which in use is closest to the wrist.

As used herein, the term "distal" when used to describe the finger guard defines an end of the finger guard opposite of the proximal end, or in other words, the end of the finger guard which in use is closest to the nail of the fingers and thumb.

As used herein, the term "lateral" when used to describe the finger guard defines the sides of the finger guard which in use extend parallel to the joints of the finger or thumb between and interconnecting the proximal end and distal end of the finger guard.

By way of introduction, the subject disclosure is related to apparatuses and methods for assembling apparatuses related to protecting fingers, thumbs, and/or hands from injuries including, but not limited to, hyperextension and other injuries resulting from impact collisions to the finger, thumb, and/or hand. In an aspect, an apparatus is provided that protects fingers by providing an exoskeleton like structure to the finger and also allowing the finger the ability to move according to the typical range of motion (e.g., bending, curling, stretching, etc.) associated with a finger and its respective joints.

Furthermore, in an aspect, the apparatus comprises a series of hinges that allow for the free and natural movement (e.g., bending) of fingers while wearing the apparatus. The hinges are strategically positioned at regions of the apparatus that facilitate natural movement of finger joints (e.g., allowing for bending, flexing, and extending) and corresponding finger segments. Also, in an aspect, the apparatus can both allow the finger to perform a range of movements and motions typical of a finger, while also providing a protective shield to the exterior of the finger to defend against damage from high-impact collisions. Furthermore, in an aspect, the apparatus comprises a hinge mechanism that can act as a governor that locks the apparatus from bending past a maximum degree of bend. In an aspect, the facility of the apparatus to limit bending of a finger past a particular point protects against an occurrence of injuries related to unnatural finger bending movements such as hyperextension and other bending-related injuries.

Referring now to FIG. 1 illustrated is a non-limiting high-level diagram of a perspective view of an an example apparatus (e.g., referred to as finger brace 10) configured to protect a finger and/or thumb, wherein the apparatus is positioned in a first position in accordance with one or more embodiments described herein. In an aspect, the reference numerals are used to identify similar elements throughout the several views of a finger guard apparatus shown in FIG. 1 and generally designated at reference numeral 10.

In an aspect, FIG. 1 illustrates a perspective view of finger guard 10. In an aspect, the various elements and components of finger guard 10 shown in FIG. 1 include, but are not limited to, proximal component 12, intermediate component 14, distal component 16, first hinge component 18, second hinge component 20, first set of openings 22, and/or plate component 24. In an aspect, FIG. 1 illustrates a non-limiting embodiment of finger guard 10 that can include all the components and elements described in other embodiments described herein.

In an aspect, finger guard 10 can comprise a first hinge component 18 configured to connect a proximal component 12 configured to fit around at least a first portion (e.g., finger segment such as a proximal phalanx) of a finger near a wrist to an intermediate component 14 located at a central portion of the apparatus (e.g., finger guard 10), wherein the proximal component 12 is located at a lateral portion of the apparatus. In an aspect, the first hinge component 18 can comprise an integration between a peg receiving portion 191 that extends from an end portion of the proximal component 12 and a first peg protruding from the intermediate component 14. Furthermore, the peg receiving portion 191 can be configured with a rounded semicircle outer edge 193 of the peg receiving portion 191 and can circumscribe the first peg 193 to facilitate a pivoting movement of the proximal component 12 and the intermediate component 14 around the first hinge component 18. As such, the peg receiving portion 191 is configured to act as a first pivot element and the first peg is configured to act as a second pivot element of the first hinge component 18.

In another aspect, finger guard 10 can comprise a second hinge component 20 configured to connect the intermediate component 14 (e.g., configured to fit around a finger segment such as a middle phalanx) of the apparatus to a distal component 16 configured to fit around at least a second portion (e.g., finger segment such as a distal phalanx) of the finger near a finger nail, wherein the distal component 16 is located at a distal portion of the apparatus. In an aspect, the second hinge component 20 can comprise an integration between another peg receiving portion that extends from an end portion of the intermediate component 14 and a second peg protruding from the distal component 16.

In an aspect, finger guard 10 can be an elongated apparatus substantially symmetric about its longitudinal axis, meaning that, in a non-limiting embodiment, the configuration of the right side and left side of finger guard 10 can be identical. The finger guard 10 can comprise three individual components, a proximal component 12, an intermediate component 14 and a distal component 16. In an aspect, the proximal component 12, intermediate component 14, and distal component 16 of finger guard 10 can be connected by two hinge systems, each respective hinge system comprising a pair of hinges 18 (e.g., also referred to as first hinge component 18 or proximal hinge system 18) and 20 (e.g., also referred to as second hinge component 20 or distal hinge system 20). In an aspect, proximal component 12, intermediate component 14, and distal component 16, respectively exhibit significant dome-like curvatures in traverse cross-section (i.e., curvature which is curved in more than one direction).

In an aspect, the proximal component 12 can comprise a first dome-shaped curvature and a first set of openings. In another aspect, the distal component 16 comprises a second dome-shaped curvature and a second opening, and wherein a connection between the intermediate component 14 and the distal component 16 form a third opening. In an aspect, the dome-like curvature of the proximal component 12, intermediate component 14, and distal component 16 of finger guard 10 allows for the finger or thumb to fit comfortably within the confines of the finger guard 10 casing. As such, the dome-like curvature of respective finger guard 10 components align to the curvature of respective fingers on a hand.

In another aspect, one or more embodiment can provide an adjusted curvature of proximal component 12, intermediate component 14, and/or distal component 16 to fit the profile of a user finger. As such, a customized finger guard 10 can be provided for a range of users having fingers of differing curvatures, thickness, and width. In another non-limiting embodiment, finger guard 10 can be formed out of a material (e.g., plastic) that can be molded into the shape of a user finger. For instance, a user can receive a version of the finger guard that comprises the framework component parts of finger guard 10 such as the proximal component 10, intermediate component 14, distal component 16, first hinge component 18, and second hinge component 20. In an aspect, a user can utilize a box encasing comprising a material formed as a hand shape and capable of receiving a user hand. As heat is applied to the material (e.g., through the box, on the outside of the box), the material molds to the user hand and can form the finger brace customized to such user's fingers.

However, in such non-limiting embodiment, the finger guard can be loose fitting until a customized fitting process occurs to adjust the finger guard to the contours of the user. For instance, the loose-fitting finger guard and its compositional material (e.g., plastic) can be warmed and heated until soft. Furthermore, the soft plastic finger guard can be vacuum formed over the user hand or a model of the user hand to fit in a customized manner to the contours and specifications of the user finger. In another aspect, the finger guard 10 that is not customized to fit the target user fingers in a snug manner can be hardened using a drying process.

In another non-limiting embodiment, a user can provide a model of his/her hand and utilize thermal pressure, high temperature heating, and/or other customization techniques to adjust the fit of the finger guard to a user's specifications. In yet another non-limiting embodiment, finger guard 10 can be comprised of different sized component parts available to mix and match to form the correct fitted size per a target user. As such, a proximal component 12 segment of a first size, an intermediate component 14 of a second size, and a distal component 16 of a third size can be varied and such sizes can be interchanged based on the needs of a user.

Furthermore, in an aspect, pre-sized standardized finger guard 10 can be manufactured and provided in a fully assembled format as well. Accordingly, in an aspect, the proximal components 12, intermediate component 14 and distal component 16 of finger guard 10 (and other embodiments) are structured and designed to fit the natural contours of one or more finger. In another aspect, the lengths of the proximal component 12, intermediate component 14, and distal component 16 respectively can vary in size, and be sized to fit various finger or thumb sizes of a user. For instance, the proximal component 12 can have a first length that is greater than the intermediate component 14, and wherein the intermediate component 14 can have a second length that is greater than the distal component 16.

As such, in an instance, a user with a longer distal phalanges portion can utilize a finger guard 10 with a longer distal component 16. In another aspect, a user having a shorter middle phalanges may utilize a finger guard 10 with a shorter intermediate component 14. Furthermore, in an aspect, a user having a longer proximal phalanges can utilize a finger guard 10 with a longer proximal component 12. In another aspect, finger guard 10 can include customized size settings to allow for variations in finger circumferences at various regions of the finger. For instance, if a user has a finger with a greater circumference, then a wider dome-like curvature of proximal component 12, intermediate component 14, and/or distal component 16 can be available for use.

In a non-limiting embodiment, proximal component 12, intermediate component 14, and distal component 16 can correspond to the natural structure of anatomical segments of the finger or thumb, wherein the proximal component 12 can be the longest in length, followed by the intermediate component 14 (e.g., length shorter than proximal component 12 and longer than distal component 16), and then the distal component 16 (e.g., shortest in length). In an aspect, a non-limiting embodiment of finger guard 10 following this anatomical pattern, can enable the finger guard hinge systems (e.g., proximal hinge system 18 distal hinge system 20) to align with a finger or thumb joint, such that the finger guard 10 mimics the natural movement of the finger or thumb.

In another aspect, the proximal component 12 and the intermediate component 14 of the finger guard 10 have cut-out elliptical openings (e.g., referred to as openings 22) to allow for the movement of air through the finger guard 10. In an aspect, such movement of air through the finger guard 10 can give an inserted individual finger or thumb breathability and reduce risks of a finger or thumb overheating. In other embodiments, the openings 22 can include shapes other than an elliptical (e.g., rectangles, diamonds, etc.) or comprise one or more elliptical of various dimensions (e.g., wider, longer, narrower, etc.). Also, in a non-limiting embodiment, the openings can be of different sizes such that an opening (E.g., referred to as second opening) between and formed from the interlocking arrangement of proximal component 12 and intermediate component 14 can be larger than the opening (e.g., referred to as third opening) between and formed by the integration of intermediate component 14 and distal component 16.

In an aspect, the size of the openings can be varied to accommodate the size and shape of respective finger knuckles. Furthermore, the openings allow the knuckles to carry out its typical movement (e.g., bending) patterns by providing enough room for such knuckles to fold and extend. Accordingly, in an instance, the second opening can accommodate the motion of a proximal interphalangeal joint (e.g., middle knuckle) and the third opening can accommodate the motion of a distal interphalangeal joint (e.g., top knuckle). Furthermore, in an aspect, finger guard 10 and the proximal component 12 leaves space for the base knuckle to carry on its typical range of motion. As such, in an instance, a third opening can be larger than a second opening.

In another aspect, finger guard 10 can comprise a first set of openings 22. In an aspect, these openings can be shape as oval openings along the top of proximal component 12 and/or intermediate component 14 to allow for air circulation and flow to the finger while wearing finger guard 10. It is also possible to modify the function of the finger guard 10 by selectively arranging the first set of openings 22 in defined spacing arrangements of finger guard 10. In another aspect, first set of openings 22 can also influence the bending properties of finger guard 10. For instance, a greater number of openings or greater size of such openings can facilitate greater malleability of such portions of finger guard 10. In an aspect, an optimal arrangement of openings 22 can be determined, as an efficacious determination of materials, and shape of finger guard 10 and its components can be determined using a finite-element-analysis. For instance, finger guard 10 and its various dimensions and compositions in respective embodiments can undergo an analysis to predict the behavior of finger guard 10 under duress imposed by various impacts (e.g., mechanical stress, heat transfer, mechanical vibrations, structural analysis, injection molding, etc.)

In another aspect, as briefly described above, finger guard 10 can comprise two pairs of revolute joints (e.g., proximal hinge system 18 distal hinge system 20), wherein each joint attaches to the ends of two of the finger guard components (e.g., proximal component 12, intermediate component 14, and distal component 16). In a non-limiting embodiment, the distal end of the proximal component 12 and the proximal end of intermediate component 14 may be formed to be of a thicker composition and flared outward at the revolute joints (e.g., proximal hinge system 18 and distal hinge system 20) so that the finger guard 10 provides space for the joints of the finger or thumb in the finger guard 10.

For instance, a finger can be anatomically wider at the joints or locations where finger segments meet. Furthermore, in an aspect, the shape of the finger may contort (e.g., get wider) as a joint performs a bending operation. As such, first hinge component 18 and second hinge component 20 can be located at a wider portion of finger guard 10 components in order to accommodate such bending motions of a finger joint. In addition to being thicker, the distal ends of the proximal component 12 and the intermediate component 14 of the finger guard 10 may be rounded, or circular, to provide flexibility and durability against high forces and stresses experienced near the joints of the finger or thumb.

In an aspect, first hinge component 18 and second hinge component 20 of finger guard 10 allow for a finger or thumb to conduct its natural movement respectively. Thus, the hinge systems mimic the bending motion of such appendages by allowing the components (proximal component 12, intermediate component 14, distal component 16) to swing freely in accordance with finger bending motions. In other non-limiting embodiments, finger guard 10 can utilize a range of suitable hinge systems, which allow the finger guard 10 to move freely about the joints of the finger and thumb, include, but not limited to, prismatic joints, screws, rivets, and spherical joints. In an aspect, a suitable hinge system can provide a sufficient range of motion to the fingers and provide different options of movement, while still protecting the fingers and thumb from impact related injuries and over extension such as hyperextension. In an aspect, first hinge component 18 and second hinge component 20 comprise hinges that allow for the finger to endure a wide range of motions, however, a plate component 24 working in connection with each respective hinge system can stop the finger guard from undergoing potentially injurious ranges of motion.

In an aspect, plate component 24 protrudes from the periphery of the intermediate component 14 of the finger guard 10. The plate component 24 can function to define a locked position of the finger guard 10 when the finger or thumb is being moved towards the dorsal aspect of the hand (or for movement towards other positions). In many cases with hyperextension, the fingers usually are moved beyond the range of motion towards the dorsal aspect of the hand. The plate component 24 can help to prevent hyperextension of the finger or thumb because it can limit bending of the intermediate component 14 of the finger guard 10 in the proximal direction.

In an aspect, plate component 24 can be adjusted to allow for stoppage of bending of apparatus 10 components to occur at varying degrees of motion. For instance, a user desiring a finger to endure a greater range of motion (e.g., 70 degree angle) of the finger can adjust the plate component 24 to stop the movement of the finger guard components after reaching a greater bending threshold. Accordingly, a finger guard 10 customized to each finger on a hand can be adjusted to have different bending restrictions for each such finger by adjusting the constraints and limitations imposed by plate component 24 on respective hinge systems.

In another aspect, plate component 24 can be fitted to accommodate various friction metrics along with the associated hinge system to limit the possibility of hyperextension. In an aspect, plate component 24 may be a triangular shape or shape other than a triangle, such as, for example, a rectangle, hexagon, pentagon, or other shape that functions to create a stopper to the finger brace after bending beyond a target angle. In some embodiments, plate component 24 can have at least three sides and at least three angles (e.g., triangle). In addition, a plurality of plates may be used adjacent to the hinge systems to prevent the fingers and thumb from hyperextending in the dorsal direction. In other embodiments, plate component 24 can be fitted to work in connection with either or both of hinge component 18 and/or hinge component 20. Furthermore, in other embodiments, plate component 24 can be employed on either one or both sides of finger guard 10. In a non-limiting embodiment, plate component 24 can be employed on both sides of only first hinge component 18.

Figure 2:
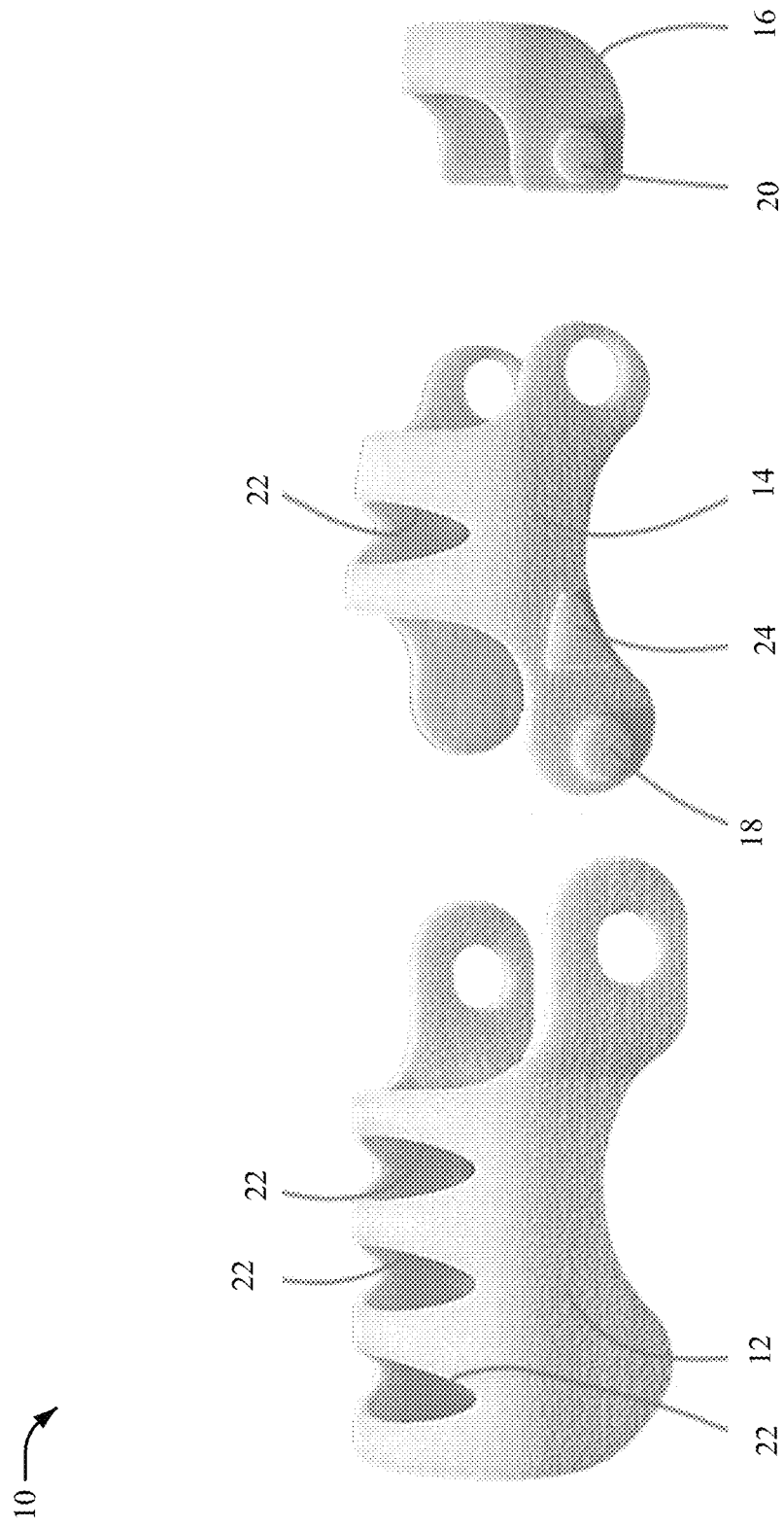
FIG. 2 illustrates a non-limiting high-level diagram of a perspective view of a non-limiting example apparatus configured to protect a finger and/or thumb, wherein the apparatus components are detached into segmented parts in accordance with one or more embodiments described herein.

Turning now to FIG. 2, illustrated is a non-limiting high-level diagram of a perspective view of an example apparatus configured to protect a finger and/or thumb, wherein the apparatus components are detached into segmented parts in accordance with one or more embodiments described herein. Repetitive description of like elements employed in other embodiments described herein is omitted for sake of brevity.

In an aspect, FIG. 2 illustrates a perspective exploded view of finger guard 10 with the components broken into several segments. In an aspect, the various elements and components of finger guard 10 shown in FIG. 2 include, but are not limited to, proximal component 12, intermediate component 14, distal component 16, first hinge component 18, second hinge component 20, first set of openings 22, and/or plate component 24.

In an aspect, the exploded view of the proximal component 12, intermediate component 14, and distal component 16 illustrated as separate segments demonstrates the ability to vary the size and/or shape of each component part of finger guard 10. Accordingly, the proximal component 12, intermediate component 14, and distal component 16 can be of different sizes to provide a customized fit to a user. Furthermore, the components can be interchanged such that a new individual part can be integrated with older existing component parts to provide a functional finger guard 10 without the need to obtain an entirely new set of components. In another aspect, the hinge mechanisms of first hinge component 18 and second hinge component 20 are illustrated. For instance, the male hinge components (first hinge component 18 and second hinge component 20) can be fitted within the female openings in intermediate component 14 and proximal component 12 respectively to create a bendable and pivotable hinge mechanism.

Figure 3:
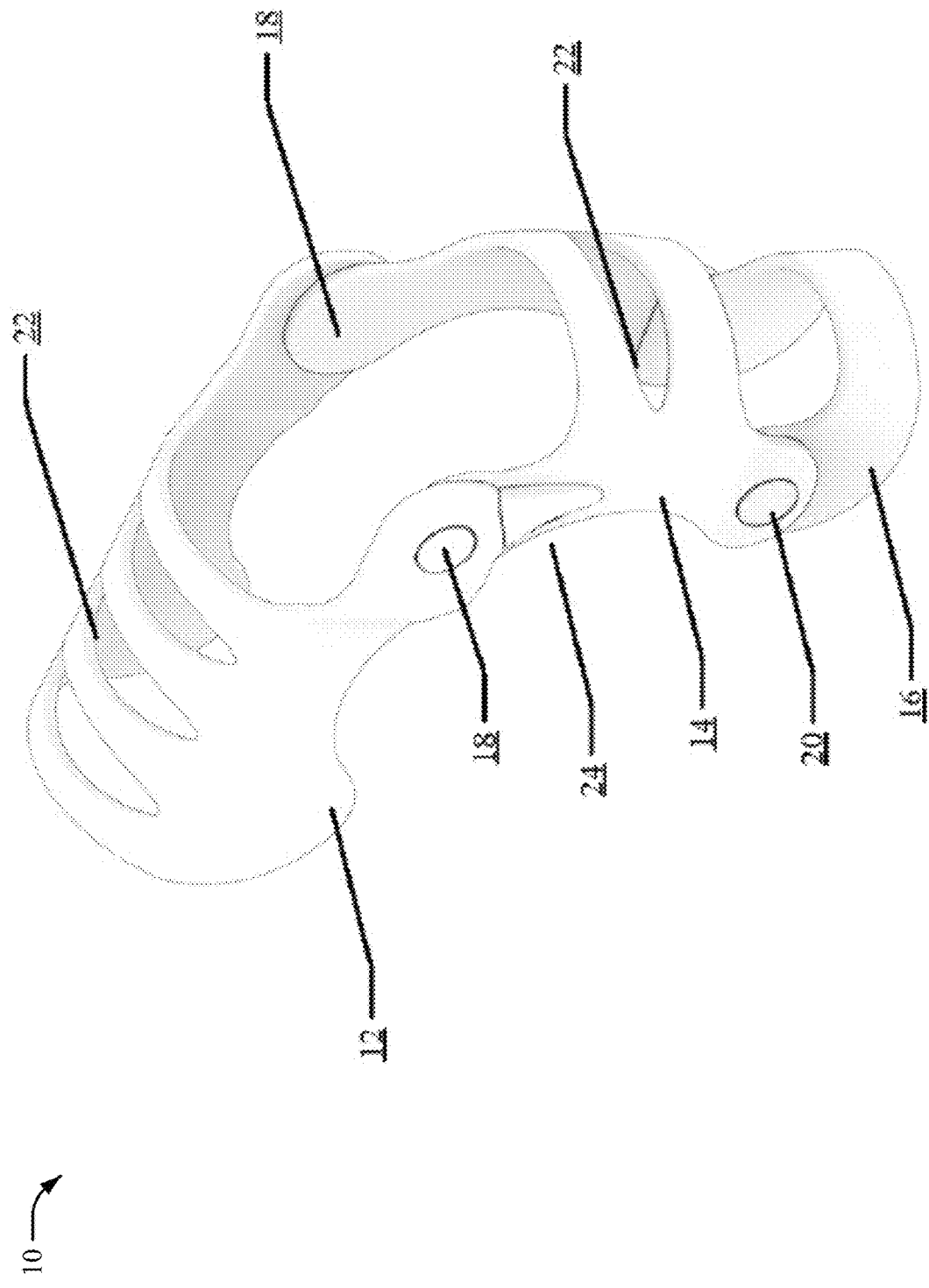
FIG. 3 illustrates a non-limiting high-level diagram of a perspective view of a non-limiting example apparatus configured to protect a finger and/or thumb, wherein the apparatus is positioned in a second position in accordance with one or more embodiments described herein.

Turning now to FIG. 3, illustrated is a non-limiting high-level diagram of a perspective view of an example apparatus configured to protect a finger and/or thumb, wherein the apparatus is positioned in a second position in accordance with one or more embodiments described herein. Repetitive description of like elements employed in other embodiments described herein is omitted for sake of brevity.

In an aspect, FIG. 3 illustrates a perspective view of finger guard 10 adjusted into a second position. In an aspect, the various elements and components of finger guard 10 shown in FIG. 3 include, but are not limited to, proximal component 12, intermediate component 14, distal component 16, first hinge component 18, second hinge component 20, first set of openings 22, and/or plate component 24.

In an aspect, FIG. 3 shows finger guard 10 bending along the first hinge component 18 and the second hinge component 20. In an aspect, each pair of hinges (e.g., proximal hinge system 18 and distal hinge system 20) allows the associated proximal component 12, intermediate component 14, and distal component 16 to bend at least 90 degrees along the axis of rotation of a finger joint, and to bend independently of one another, ultimately allowing for the finger to achieve natural bending movement. In addition, the hinge systems of the finger guard 10 provide the joints of the finger and thumb with protection against high impact forces experienced on the lateral sides of the finger and thumb. For instance, football players experience high impact forces from shoulder pads and helmets on the joints of the fingers and thumb. Thus, the hinge system can offer a noteworthy degree of protection of the finger and thumb joints. In an aspect, finger guard 10 can protect fingers and thumbs from contusions, hyperextensions, finger jamming, finger torsion, finger compression, and other such impact-related finger injuries.

Figure 4:
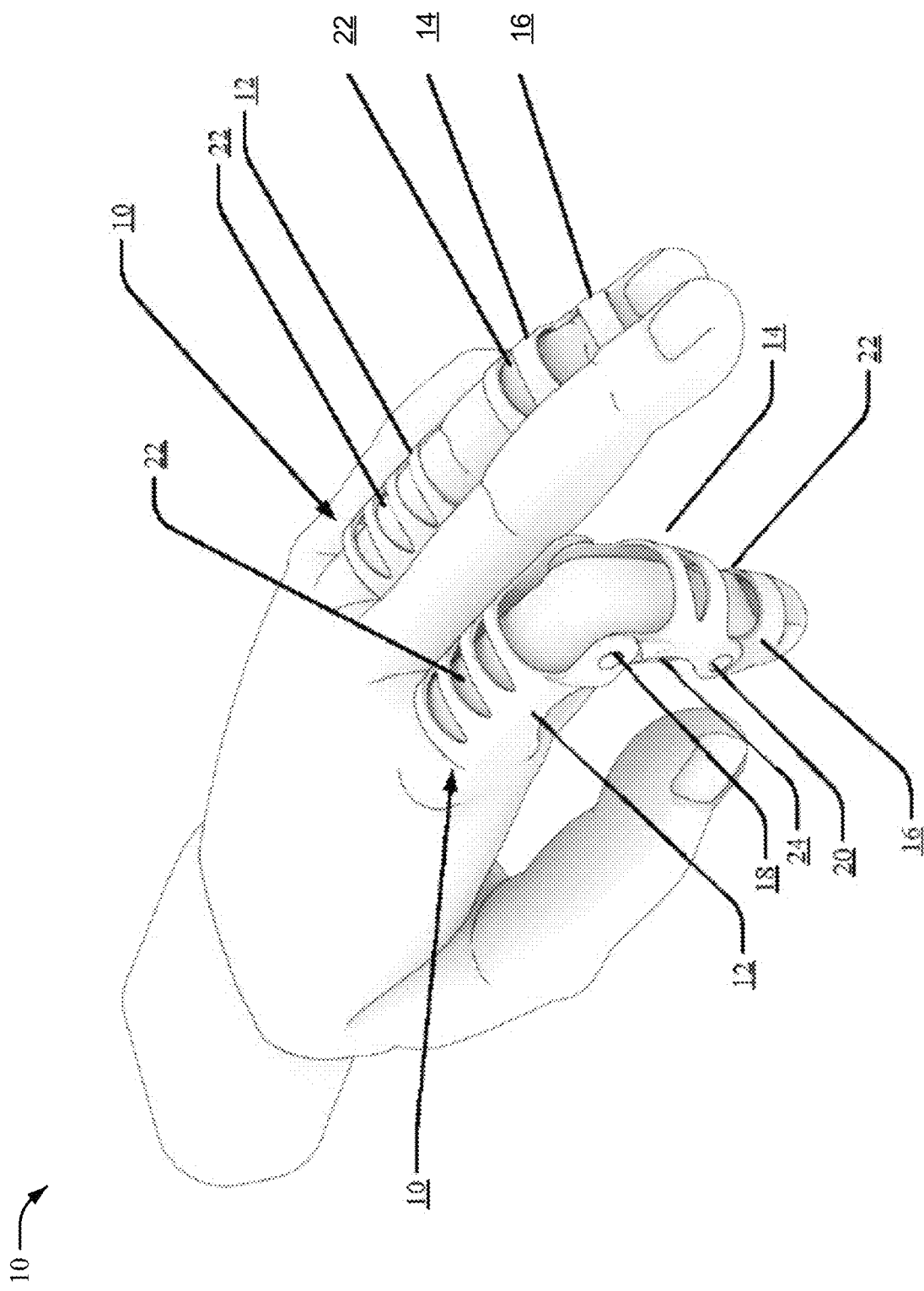
FIG. 4 illustrates a non-limiting high-level diagram of a perspective view of a non-limiting example apparatus configured to protect a finger and/or thumb, wherein the apparatus is positioned in a second position and shown to be worn on a pointer finger and positioned in a first position and shown to be worn on a ring finger of a left hand in accordance with one or more embodiments described herein.

Turning now to FIG. 4, illustrated is a non-limiting high-level diagram of a perspective view of an example apparatus configured to protect a finger and/or thumb, wherein the apparatus is positioned in a second position and shown to be worn on a pointer finger and positioned in a first position and shown to be worn on a ring finger of a left hand in accordance with one or more embodiments described herein. Repetitive description of like elements employed in other embodiments described herein is omitted for sake of brevity.

In an aspect, FIG. 4 illustrates a perspective view of finger guard 10 adjusted into a second position and worn on an index finger (second position) and ring finger (first position). In an aspect, the various elements and components of finger guard 10 shown in FIG. 4 include, but are not limited to, proximal component 12, intermediate component 14, distal component 16, first hinge component 18, second hinge component 20, first set of openings 22, and/or plate component 24.

In an aspect, FIG. 4 shows the bending nature of the finger guard 10 wherein all three of proximal component 12, intermediate component 14, and distal component 16 of the finger guard 10 are capable of bending about the pairs of hinges (e.g., proximal hinge system 18 and distal hinge system 20) in accordance with natural bending motions of respective fingers.

For instance, the proximal hinge system 18 can restrict an over bending from occurring at the proximal interphalangeal joint (PIP) in the middle of the finger by locking the finger brace 10 and/or 30 in place after a certain amount of bending has occurred. As such, the locking mechanisms of proximal hinge system 18 prevents over extension of a finger and can prevent injuries associated with such finger over extension.

In an aspect, the proximal hinge system 18 can be symmetrically situated on either side of an overlapping region between the proximal component 12 and the intermediate component 14. In another aspect, the distal hinge system 20 comprises two hinges symmetrically situated on either side of an overlapping region between the intermediate component 14 and the distal component 16.

Again, the distal hinge system 20 like the proximal hinge system 18 can restrict a bending motion of finger guard 10 and/or 30 after a certain degree of bending has occurred in order to prevent finger injuries associated with a finger over extension. For instance, distal hinge system 20 (comprising a pair of hinges) can restrict the finger form over-extending at a distal interphalangeal joint of a finger, by restricting the hinge from bending after a maximum degree of bending has occurred. In an aspect, the hinge mechanism of distal hinge system 20 comprises a plate that interfaces with the hinge, such that after a certain degree of bending has occurred at the hinge or joint, the plate is positioned in a manner that blocks the hinge from bending any further. In an aspect, the plate can be a triangle where a first side is flush with a curved portion of the distal hinge system 20, a second side is perpendicular to the first side. As such, upon a bending of distal hinge system 20 to a maximum level, the second side of plate 24 becomes flush with the distal hinge system 20 to prevent any further bending of the intermediate component 14 of finger guard 10.

Figure 5:
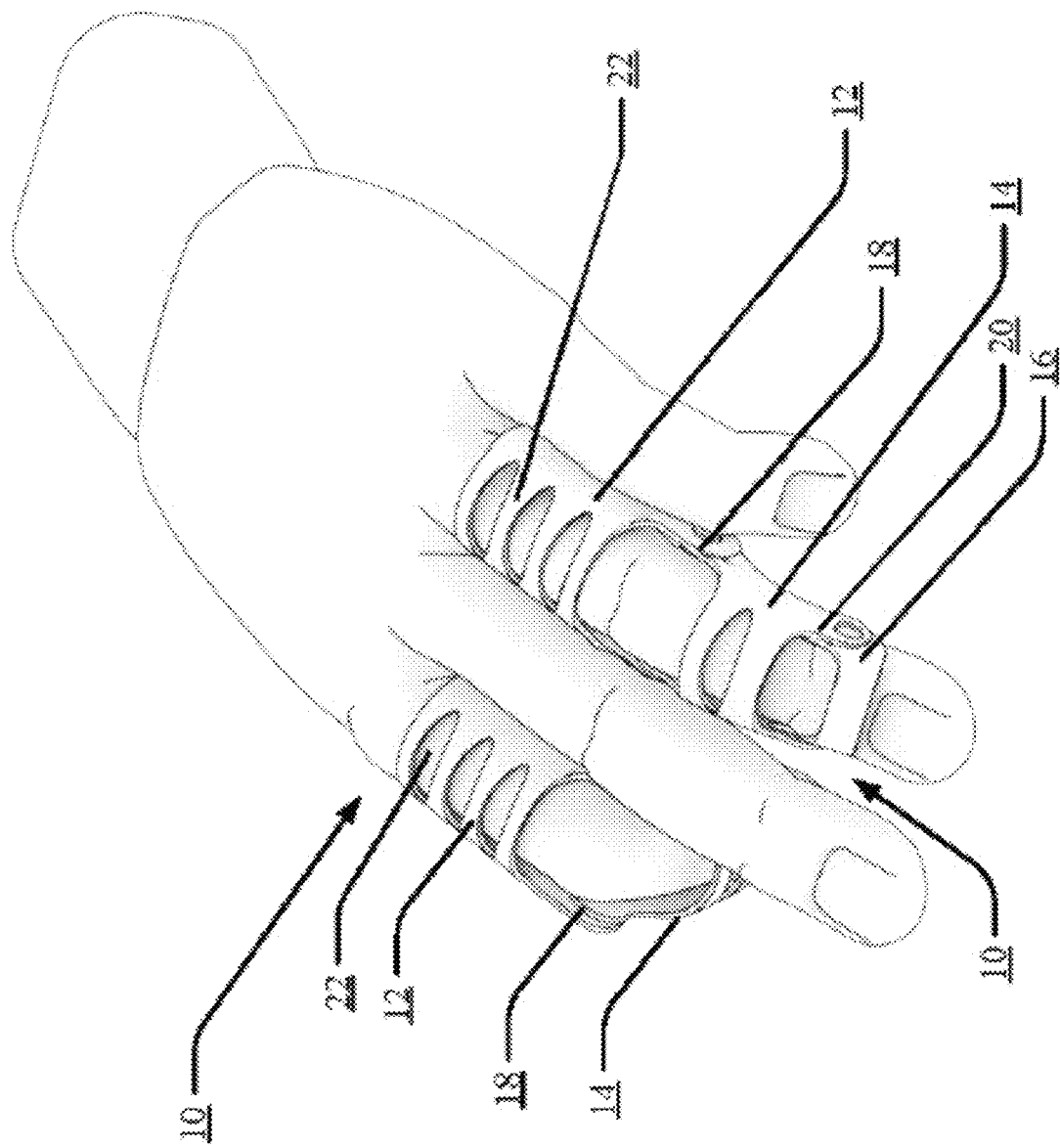
FIG. 5 illustrates a non-limiting high-level diagram of a top left perspective view of an example apparatus configured to protect a finger and/or a thumb, wherein the apparatus is positioned in a second position and shown to be worn on a pointer finger and positioned in a first position and shown to be worn on a ring finger of a left hand in accordance with one or more embodiments described herein.

Turning now to FIG. 5, illustrated is a non-limiting high-level diagram of a top left perspective view of an example apparatus configured to protect a finger and/or a thumb, wherein the apparatus is positioned in a second position and shown to be worn on a pointer finger and positioned in a first position and shown to be worn on a ring finger of a left hand in accordance with one or more embodiments described herein. Repetitive description of like elements employed in other embodiments described herein is omitted for sake of brevity.

In an aspect, FIG. 5 illustrates a perspective view of finger guard 10 adjusted into a second position. In an aspect, the various elements and components of finger guard 10 shown in FIG. 5 include, but are not limited to, proximal component 12, intermediate component 14, distal component 16, first hinge component 18, second hinge component 20, first set of openings 22, and/or plate component 24.

Repetitive description of like elements employed in other embodiments described herein is omitted for sake of brevity. In an aspect, FIG. 5 shows the bending nature of the finger guard 10 wherein all three components proximal component 12, intermediate component 14, and distal component 16 of the finger guard are able to bend about the pairs of hinges (e.g., proximal hinge system 18 and distal hinge system 20) in accordance with natural bending motions of respective fingers.

Figure 6:
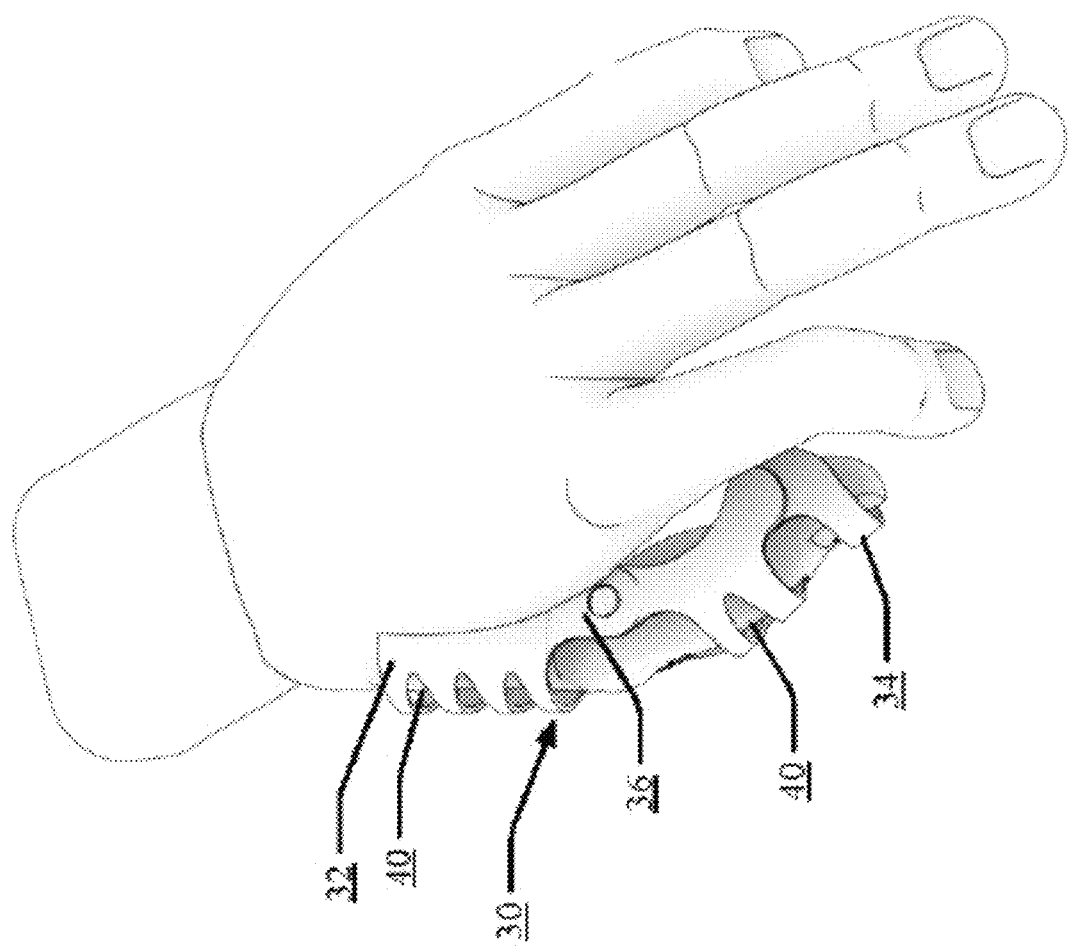
FIG. 6 illustrates a non-limiting high-level diagram of a right side perspective view of an example apparatus configured to protect a finger and/or a thumb, wherein the apparatus is positioned in a third position and shown to be worn on a thumb of a left hand in accordance with one or more embodiments described herein.

FIG. 6 illustrates a non-limiting high-level diagram of a right side perspective view of an example apparatus configured to protect a finger and/or a thumb, wherein the apparatus is positioned in a third position and shown to be worn on a thumb of a left hand in accordance with one or more embodiments described herein. Repetitive description of like elements employed in other embodiments described herein is omitted for sake of brevity. In an aspect, FIG. 6 shows an embodiment of a finger guard on a thumb of a user, generally designated at reference numeral 30. The finger guard 30 in this embodiment comprises two components, a proximal thumb component 32 and a distal thumb component 34, connected by a hinge system (e.g., pair of revolute joints 36).

In an aspect, the hinge system can comprise a pair of revolute joints 36. If needed (not shown), a protruding second plate 38 may be provided to the hinge system for protection against hyperextension as in the previous embodiment. In an aspect, proximal thumb component 32 and distal thumb component 34 of the finger guard 30 each have elliptical thumb openings 40 (e.g., can be other non-elliptical shapes as well) to allow the thumb to breath and be exposed to circulating fresh air. In an aspect, the length of the proximal thumb component 32 and distal thumb component 34 can vary in size as well, as described above.

In an aspect, finger guards 10 and/or 30 respectively can be inserted onto a finger or a thumb. The components of the finger guards 10 and/or 30 respectively, can be secured to corresponding portions of a finger or thumb with a wrapping material such as athletic tape. In an aspect, finger guards 10 and/or 30 can protect a finger and/or thumb from impact related injuries and hyperextension, while allowing for the natural bending of the fingers and thumb about the joints. In another embodiment, a connective band (not shown) may be placed around one or more of the finger guard components. The connective band can be attached to the finger guard 10 and/or 30 respectively by clipping, screwing, lateral insertion, or other releasable or non-releasable mounting techniques. The connective band keeps the finger guard 10 and/or 30 attached to the finger or thumb, while also protecting against the parts of the hand not covered by the finger guard, including the palm and opisthenar. In an aspect, the connective band may be comprised of one or more of a combination of polymer materials, such a polyurethanes (PU), polyurea (PEUU), Latex, or rubber.

In another embodiment, a glove (not shown) can be worn over the hand including the finger guard 10 and/or 30. Accordingly, a finger guard 10 and/or 30 may be provided for each finger of the hand, as well as the thumb. The finger guard 10 and/or 30 can be inserted into the gloves or clothing to protect a finger from injury in a variety of sports. In an aspect, the glove can enhance and facilitate the ability of multiple finger guards 10 on multiple fingers to stay together such that the hand and fingers can better work as a cohesive unit. In an aspect, the glove can comprise padding on the exterior. Furthermore, in an aspect, the finger guard 10 can be fitted into standard gloves (e.g., brand name and existing gloves on the market) and/or the fitted gloves with pockets (e.g., specialty glove such as a glove with pockets customized to specially integrate finger guard 10).

Furthermore, in an aspect, finger guard 10 and/or 30 can be inserted into any one or more glove customized for use in any of several sports, including, but not limited to; football, lacrosse, boxing, motocross, rugby, cricket, skiing, snowboarding, soccer, and baseball. In an aspect, the finger guard 10 and/or 30 can also be inserted into the gloves or clothing of future sports that have impact related injuries. The finger guard 10 and/or 30 can also be used in connection with (e.g., inserted within) work-related gloves or clothing during activities configured to mitigate injury from potential injuries from impact in performing work. An example of this type of activity is construction work or other such labor intensive professions that require use of hands and fingers throughout the day. Since the finger guard 10 and/or 30 can be separated from the glove, the user may replace damaged or insufficiently stiff finger guard 10 and/or 30 components, for example, during practice, games, and work. For instance, a user can disassemble finger guard 10 components, replace intermediate component 14, and reintegrate the existing components (e.g., proximal component 12 and distal component 16) with a new intermediate component 14.

In an aspect, finger guard 10 and/or 30 may be manufactured using an injection molding technique, which is cost effective and efficacious. In another aspect, finger guard 10 and/or 30 can be manufactured using an extrusion of plastic material technique. In an aspect, both manufacturing methods require low manufacturing costs, low product weight and allow for the apparatus to be produced in different sizes using molds that vary in sizes and/or shapes for injection molding manufacturing purposes.

In an aspect, any of several suitable plastic materials can be used as a compositional material for finger guard 10 and/or 30. In an aspect, some such plastics can include thermoplastic polyurethanes (TPU) or polypropylene (PP). In another embodiment, finger guard 10 can be comprised of a carbon fiber to facilitate durability and scale down the size of the apparatus to fit inside a customized glove without noticing the presence of the apparatus. In another aspect, finger guard 10 and/or 30 can be composed of impact protection materials, such as a foam material (e.g., fine pitch open cell urethane foam) that can possess water sealing properties.

Furthermore, in an aspect, a glove that houses finger guard 10 and/or 30 can comprise a cushion, impact force materials (e.g., an outer fabric layer, an inner lining, a shock absorption layer) that facilitate shock absorbing properties, and/or a textile that incorporates silicone and provides impact protection (e.g., a layered material that provides padding that can be built up in various areas) within the finger guard or glove. Finger guard 10 and/or 30, can be comprised of any of the described materials herein and such materials are non-exhaustive of the materials for use in some embodiments of finger guard 10 and/or 30. Furthermore, the use of shape memory-materials is plausible, which can be brought back into the initial state by applying heat or the like, if the supporting function decreases after some time of use.

The finger guard 10 and/or 30 can also be manufactured by utilizing a multi-component injection molding technique to integrate more than one plastic material. For example, a harder plastic material can be used near the interconnecting areas of the proximal component 12, intermediate component 14, and distal component 16 to provide the hinge systems with more protection against lateral impact forces. Alternatively, a soft or elastic plastic material can be used for the bending areas of the proximal component 12, intermediate component 14, and distal component 16 adjacent the hinge systems to provide a lower bending resistance, especially for children's use.

Accordingly, finger guard 10 and/or 30 can comprise different material strengths, elasticity's, and hardness at different regions of the finger guard 10 and/or 30. As such, the use of different plastics and other materials at various regions of finger guard 10 and/or 30 facilitates the replication of natural movements of a finger as well as providing a restraint and/or restriction on movements of a finger that can cause injury or harm. Furthermore, in an aspect, by using a multi-component injection molding process to manufacture finger guard 10 and/or 30, numerous finger guards may be manufactured simultaneously and/or sequentially, using one or more nozzles.

Alternatively, the plastic material can be injected around separately pre-manufactured components of the finger guard 10 and/or 30. For example the interconnecting areas of the proximal component 12, intermediate component 14, and distal component 16 made from a sufficiently hard material (for example a metal or a composite material including carbon fiber) may be surrounded by a soft plastic material forming the bending area above the hinge systems of the finger guard. For example, stiffer finger guard elements can be exchanged against softer finger guard elements if a user requires less bending resistance to perform various desired activities. As such, finger guard 10 and/or 30 can be manufactured to have customized bending and stiffness features at various regions of the apparatus based on a preference of a user or the type of activity a user seeks to perform.

In addition, the finger guard 10 and/or 30 can be manufactured from a material that enhances the efficacy of the apparatus when inserted within or inside a glove or other such apparel item providing a pocket-like cavity for fitting the apparatus. For example, the finger guard 10 and/or 30 or the receptacle inside the glove can be coated with a friction-reducing material, such as a PTFE material. As such, PTFE can ensure that a glove and finger guard 10 move in a fluid and free-flowing manner as a single unit. Furthermore, the coating of such material on the finger guard 10 and/or 30 or within one or more cavity of a glove can enhance the protective characteristics of the glove and stabilizing characteristics of the finger guard 10 and/or 30 when used in combination with one another.

In another non-limiting embodiment, finger guard 10 can be utilized in a series of locked finger guards 10 to correct an injured finger. For instance, a finger that needs to be re-set after being broken can be set in a brace, where finger guard 10 acts as the brace. Furthermore, the finger guard 10 can be slowly adjusted over time to allow the finger to set in different angles until the finger has obtained its optimal functionality. Thus, the finger guard 10 can be utilized in a series of adjusted steps to properly correct an injured finger as well as protect a finger from injury. In a non-limiting embodiment, a user can purchase a set of finger braces, with each respective finger brace configured with slight adjustments to the device. For instance, a first finger brace can be utilized for a first period of time (e.g., week 1 through 6) and is configured to commence a first corrective aspect of the finger. In an aspect, a second finger brace configured to commence a second corrective aspect of the finger can be utilized for a second period of time (e.g., week 7 through week 12).

Furthermore, there can be numerous corrective braces configured to correct several incremental aspects of an injured finger for numerous periods of times. For instance, a finger brace can adjust the width of the hinges located on intermediate component 14 or the width of intermediate component 14 such that the manner in which proximal component 12, intermediate component 14, and distal component 16 are positioned and integrated with one another can be adjusted and configured to cause corrective changes to a finger over a period of time while simultaneously protecting the finger in its capacity as a finger brace (e.g., finger guard 10).

Figure 7:
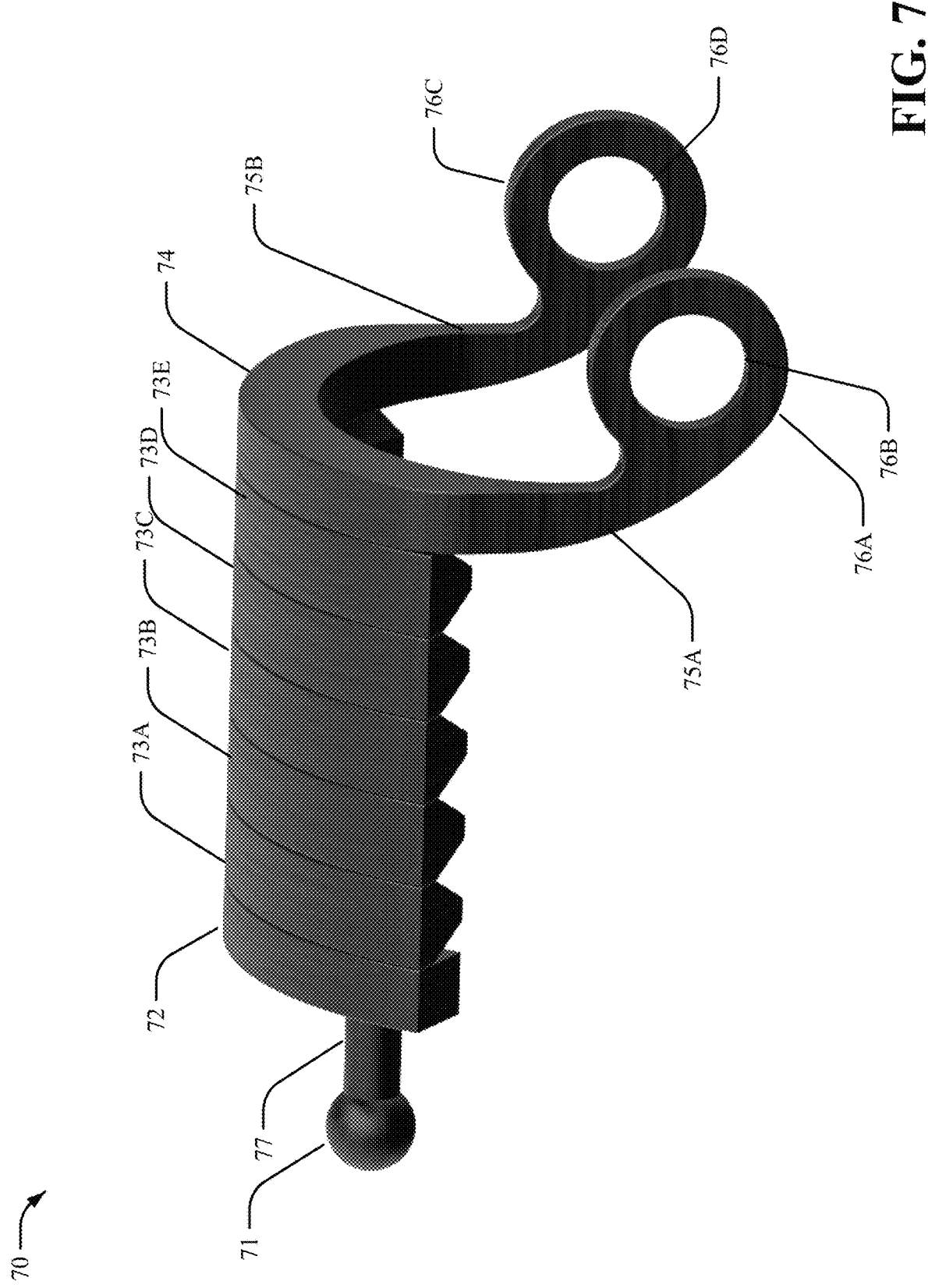
FIG. 7 illustrates a non-limiting diagram of an improved proximal component connection portion configured to connect a proximal component of a finger apparatus to a hand plate protector and configured with a ball and socket connector in accordance with one or more embodiments described herein.

FIG. 7 illustrates a non-limiting diagram of an ball joint proximal component 70 connection portion configured to connect a proximal component of a finger apparatus to a hand plate protector and configured with a ball and socket connector in accordance with one or more embodiments described herein.

At reference numeral 70 is an embodiment of a ball joint proximal component 70 of a finger brace apparatus. In an aspect, ball joint proximal component 70 comprises a ball portion 71 configured as a protruding knob or spherical object extending from a wall of the ball joint proximal component 70. Furthermore, rod portion 77 is a rod-like structure that connects ball portion 71 and a first covering portion 72. The first cover portion 72 is configured as an arched segment of ball joint proximal component 70 that connects to the rod portion 77. Also, first covering portion 72 is connected to second cover portion 73A which is connected to third cover portion 73B which is connected to fourth cover portion 73C which is connected to fifth cover portion 73D which is connected to sixth cover portion 73E which is connected to connector covering portion 74. All of the covering portions are configured as connected components that form a monolithic finger brace element that covers the phalanx portion of a finger.

Furthermore, ball joint proximal component 70 is configured to not only nestle over a portion of a finger but also integrate into other portions of a full finger and hand brace mechanism. In an aspect, ball portion 71 can interlock within a socket portion of a hand plate configured to lay over a user handle and provide a stable anchor to ball joint proximal component 70. In an aspect, ball portion 71 is configured to allow for a pivoting motion of ball joint proximal component 70 and allow for a wide range of mobility and flexibility to the finger upon which it rests. Simultaneously the ball joint proximal component 70 inhibits a flexion of the finger beyond a range that would otherwise cause hyperextension and injuries to a finger. In an aspect, such mechanism is enabled given the ball portion 71 ability to fit within a cup like depression or socket within the hand plate and likewise allow a finger to which it fits a greater range of motion. The greater range of motion can allow athletes to obtain protection against hyperextension while also providing a free range of motion or hand actions to play a sport optimally, which such actions can include gripping, squeezing, bending, pushing off, pulling, and other activities.

In another aspect, connector covering portion 74 is configured to include a first hinge arm 75A and second hinge arm 75B. In an aspect, first hinge arm 75A and second hinge arm 75B extends downward from connector covering portion 74 on both sides respectively such that they border the side walls of a finger. Furthermore, first hinge arm extends into first outer circular rim portion 76A and first inner circular rim portion 76B. The first outer circular rim portion 76A circumscribes an opening created by first inner circular rim portion 76B and such opening is configured to receive a peg portion of a finger brace intermediate component 14 disclosed throughout. In another aspect, the hinge formed by connecting a peg of intermediate component 14 with the opening formed by first outer circular rim portion 76A and first inner circular rim portion 76B allows the apparatus to form a finger brace that covers the entire finger along with the connection of intermediate component 14 to distal component 16. In another aspect, second outer circular rim portion 76C and second inner circular rim portion 76D form another opening to form a connective hinve on the other side of ball joint proximal component 70.

Figure 8:
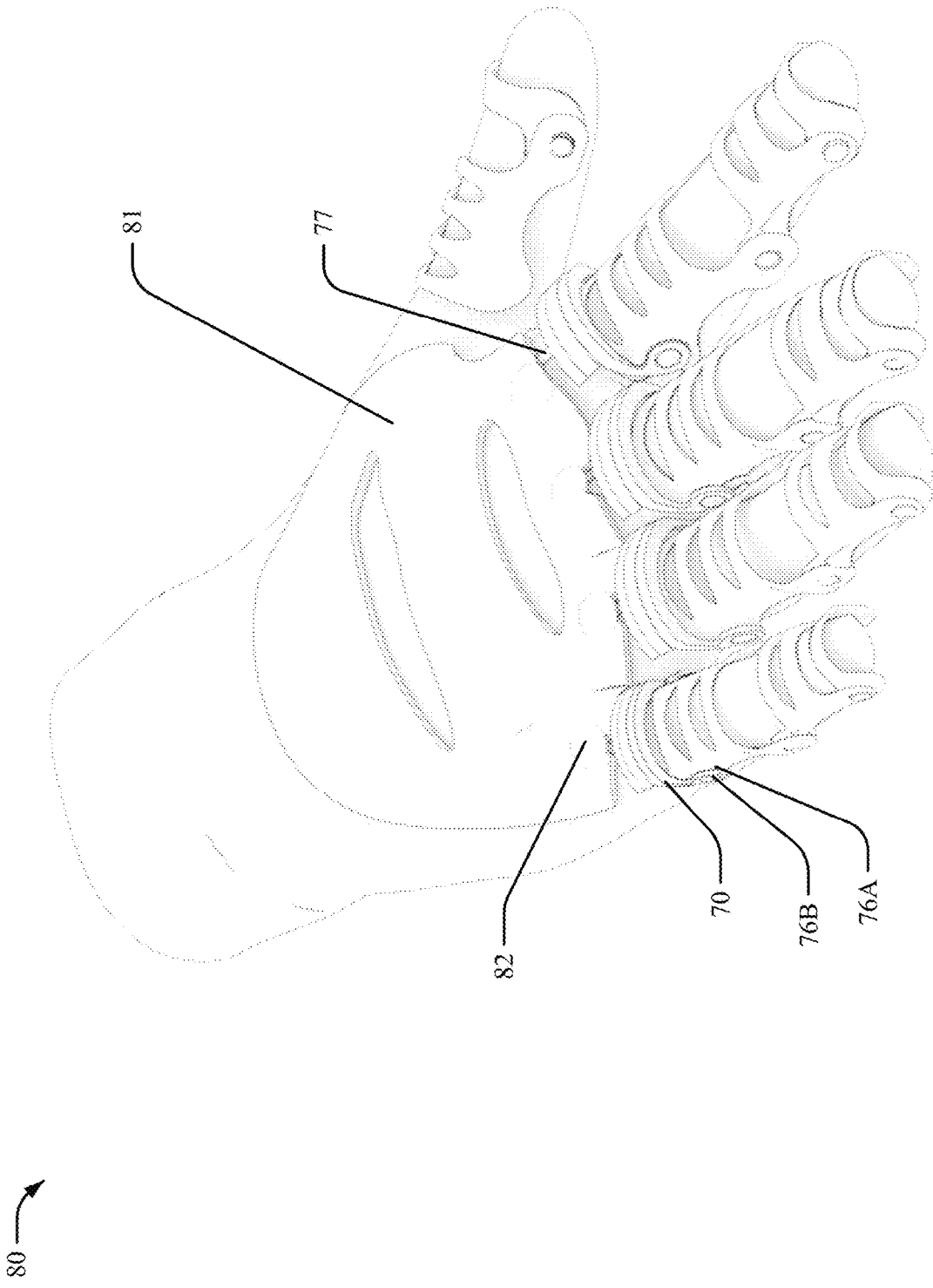
FIG. 8 illustrates a non-limiting diagram of an improved finger and hand protection apparatus and environment in accordance with one or more embodiments described herein.

Turning now to FIG. 8, illustrated is a non-limiting diagram of a finger brace apparatus connected to a hand plate mechanism via a ball and socket connection mechanism in accordance with one or more embodiments described herein.

In an aspect, environment 80 comprises a hand plate component 81, first socket portion 82, rod portion 77, ball joint proximal component 70, first outer circular rim portion 76A and first inner circular rim portion 76B. As illustrated in environment 80, the hand plate 81 is configured to rest atop of the back of a user hand and provide an anchoring mechanism to the finger and thumb brace apparatuses. Furthermore, hand plate 81 can provide a protective cover to the exterior of a hand. In an aspect, first socket portion 82 is configured to receive ball portion 71 shown in FIG. 7 to allow for a cup like encasing around the ball portion 71. As such, ball portion 71 encased by first socket portion 82 creates a integration mechanism between proximal component and hand plate 81 that allows the finger brace apparatus to pivot in a broader array of motions than traditional finger braces. Accordingly, the finger on which the brace apparatus sits can move more freely as well. Furthermore, the interface between any one or more portions of first covering portion 72, second cover portion 73A, third cover portion 73B, fourth cover portion 73C, fifth cover portion 73D to sixth cover portion 73E and/or connector covering portion 74 as well as a limitation in which the socket and rod portion allow the finger to flex backwards, prevents hyperflexion of the finger covered by the finger brace apparatus.

Figure 9:
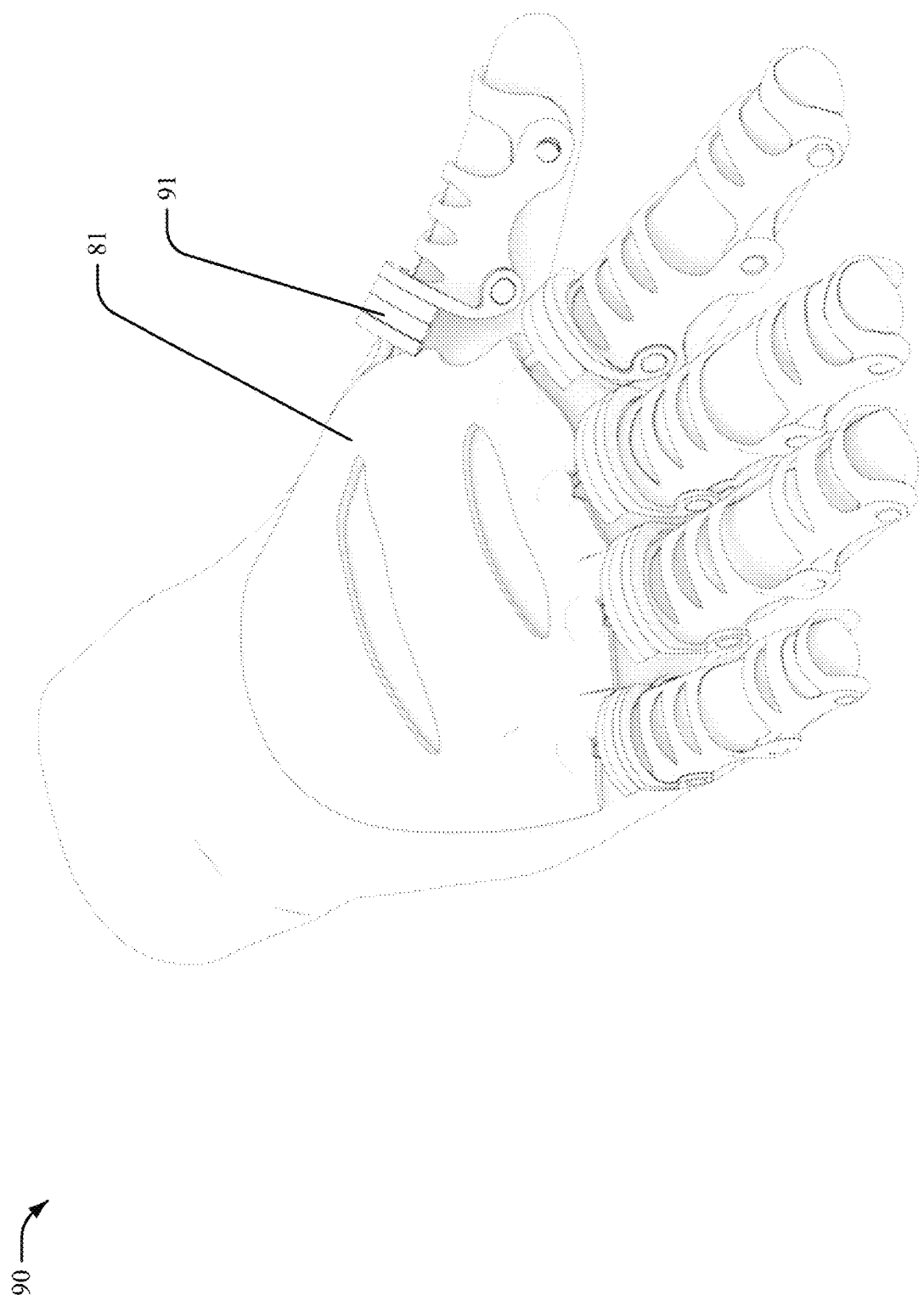
FIG. 9 illustrates a non-limiting diagram of an improved finger and hand protection apparatus and environment and thumb including a thumb connection portion in accordance with one or more embodiments described herein.

Turning now to FIG. 9, illustrated is a non-limiting diagram of an improved finger and hand protection apparatus and environment and thumb including a thumb connection portion in accordance with one or more embodiments described herein.

In an aspect, a proximal thumb component 91 is illustrated where the proximal thumb component is configured to integrate with hand plate component 81 in the same manner that the other finger brace portions connect with hand plate component 81. For instance, a rod portion is configure to provide a durable integration via a rod and socket structure that allows the thumb and proximal thumb component 91 to move in a range of motions.

Figure 10:
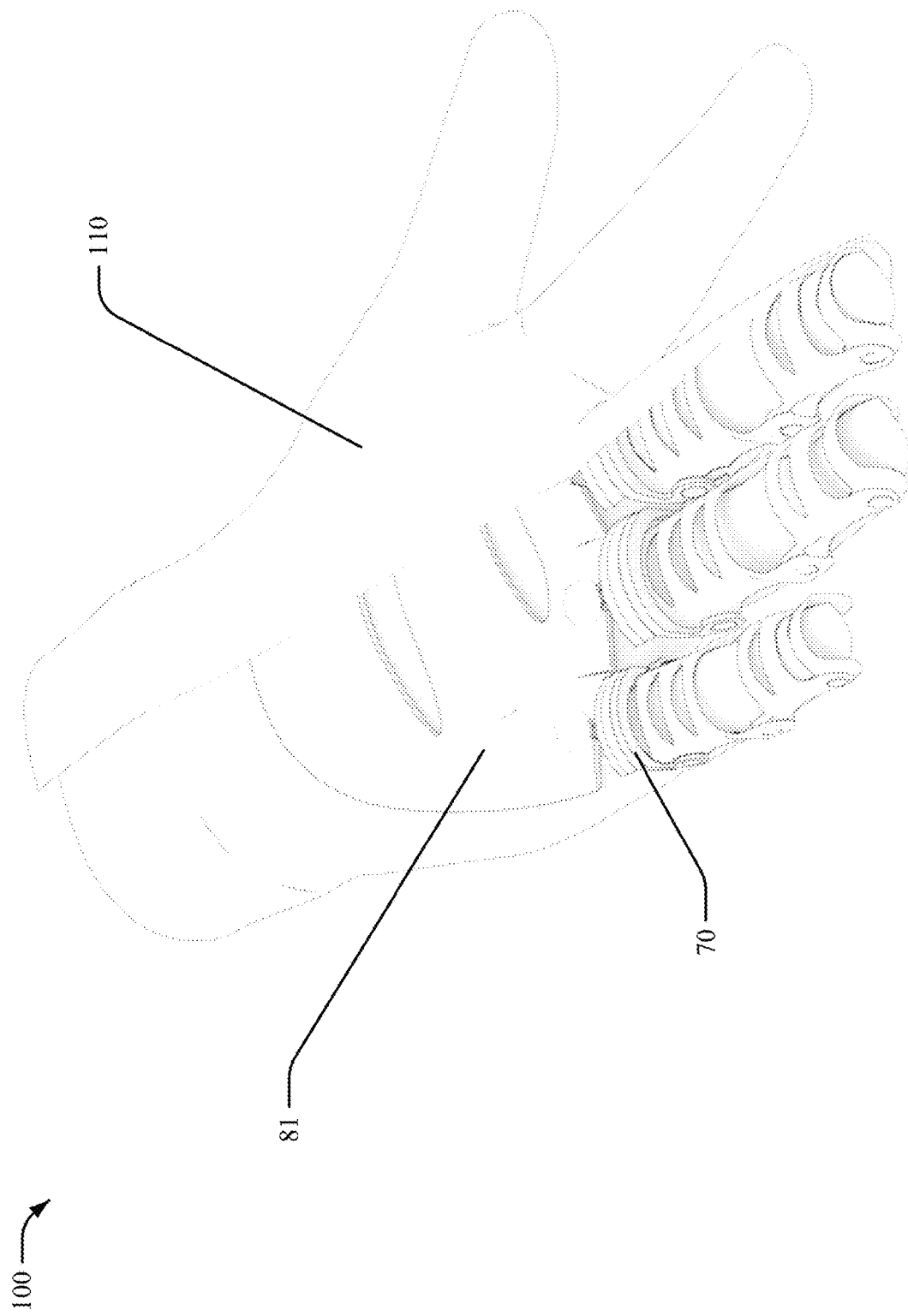
FIG. 10 illustrates a non-limiting diagram of an improved finger and hand protection apparatus within a customized glove in accordance with one or more embodiments described herein.

FIG. 10 illustrates a non-limiting diagram of an improved finger and hand protection apparatus within a customized glove in accordance with one or more embodiments described herein. In an aspect, the glove can comprise pockets or bands on the inside configured to encase each finger brace apparatus and stabilize such braces within the glove.

Figure 11:
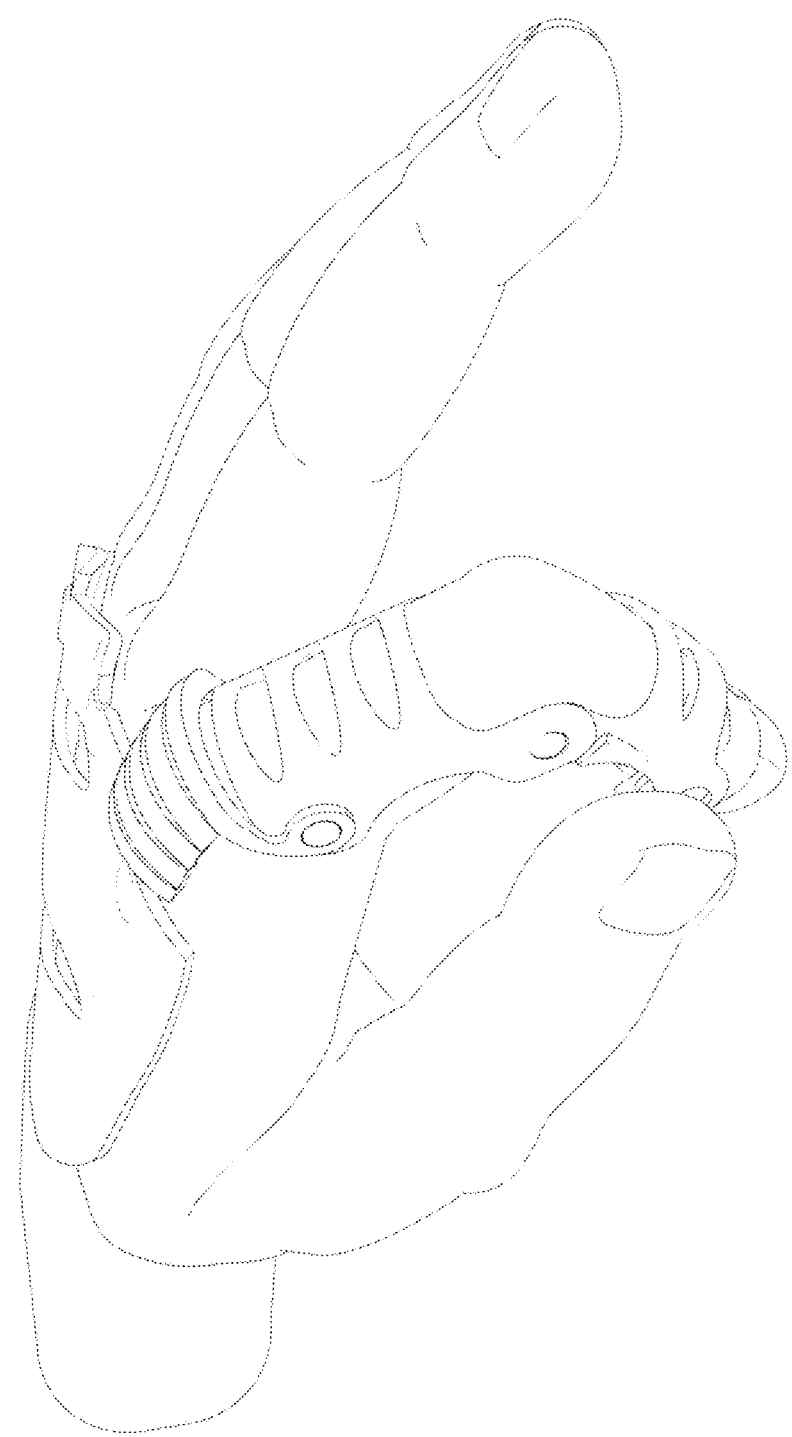
FIG. 11 illustrates a non-limiting diagram of an improved finger and hand protection apparatus in accordance with one or more embodiments described herein.

FIG. 11 illustrates a non-limiting diagram of an improved finger and hand protection apparatus in accordance with one or more embodiments described herein. In an aspect, a side view of the finger brace apparatus is disclosed at reference numeral 1100 on FIG. 11. Furthermore, FIG. 1100 includes hand plate component 81 and ball joint proximal component 70.

FIG. 12 illustrates a flow diagram of an example, non-limiting method 1200 that facilitates an assembly of a finger brace apparatus in accordance with one or more embodiments described herein. Repetitive description of like elements employed in other embodiments described herein is omitted for sake of brevity. In some implementations, at reference numeral 1202, a proximal component of an apparatus (e.g., apparatus 10) can be connected to a proximal component of a finger brace apparatus, configured to fit around at least a first portion of a finger near a wrist, to an intermediate component located at a central portion of the finger brace apparatus, wherein the proximal component is located at a lateral portion of the finger brace apparatus. At 1204, the intermediate component can be connected to a distal component of the finger brace apparatus configured to fit around at least a second portion of the finger near a fingernail, wherein the distal component is located at a distal portion of the apparatus.

FIG. 13 illustrates a flow diagram of an example, non-limiting assembly method 1300 that facilitates an assembly of a finger brace apparatus in accordance with one or more embodiments described herein. Repetitive description of like elements employed in other embodiments described herein is omitted for sake of brevity. In some implementations, at reference numeral 1302, a proximal component of an apparatus (e.g., apparatus 10) can be connected to a proximal component of a finger brace apparatus, configured to fit around at least a first portion of a finger near a wrist, to an intermediate component located at a central portion of the finger brace apparatus, wherein the proximal component is located at a lateral portion of the finger brace apparatus.

At 1304, the intermediate component can be connected to a distal component of the finger brace apparatus configured to fit around at least a second portion of the finger near a fingernail, wherein the distal component is located at a distal portion of the apparatus. At 1306, the finger brace apparatus can be locked, using a plate component 24 located adjacent to a first hinge of the finger brace apparatus, to preclude a bending of the finger brace apparatus beyond a target angle.

FIG. 14 illustrates a flow diagram of an example, non-limiting assembly method 1400 that facilitates an assembly of a finger brace apparatus in accordance with one or more embodiments described herein. Repetitive description of like elements employed in other embodiments described herein is omitted for sake of brevity. In some implementations, at reference numeral 1402, a proximal component of an apparatus (e.g., apparatus 100) can be connected to a proximal component of a finger brace apparatus, configured to fit around at least a first portion of a finger near a wrist, to an intermediate component located at a central portion of the finger brace apparatus, wherein the proximal component is located at a lateral portion of the finger brace apparatus.

At 1404, the intermediate component can be connected to a distal component of the finger brace apparatus configured to fit around at least a second portion of the finger near a fingernail, wherein the distal component is located at a distal portion of the apparatus. At 906, the finger brace apparatus can be locked, using a plate component 24 located adjacent to a first hinge of the finger brace apparatus, to preclude a bending of the finger brace apparatus beyond a target angle. At 1408, the finger brace apparatus can be connected with another finger brace apparatus via a band.

Figure 15:
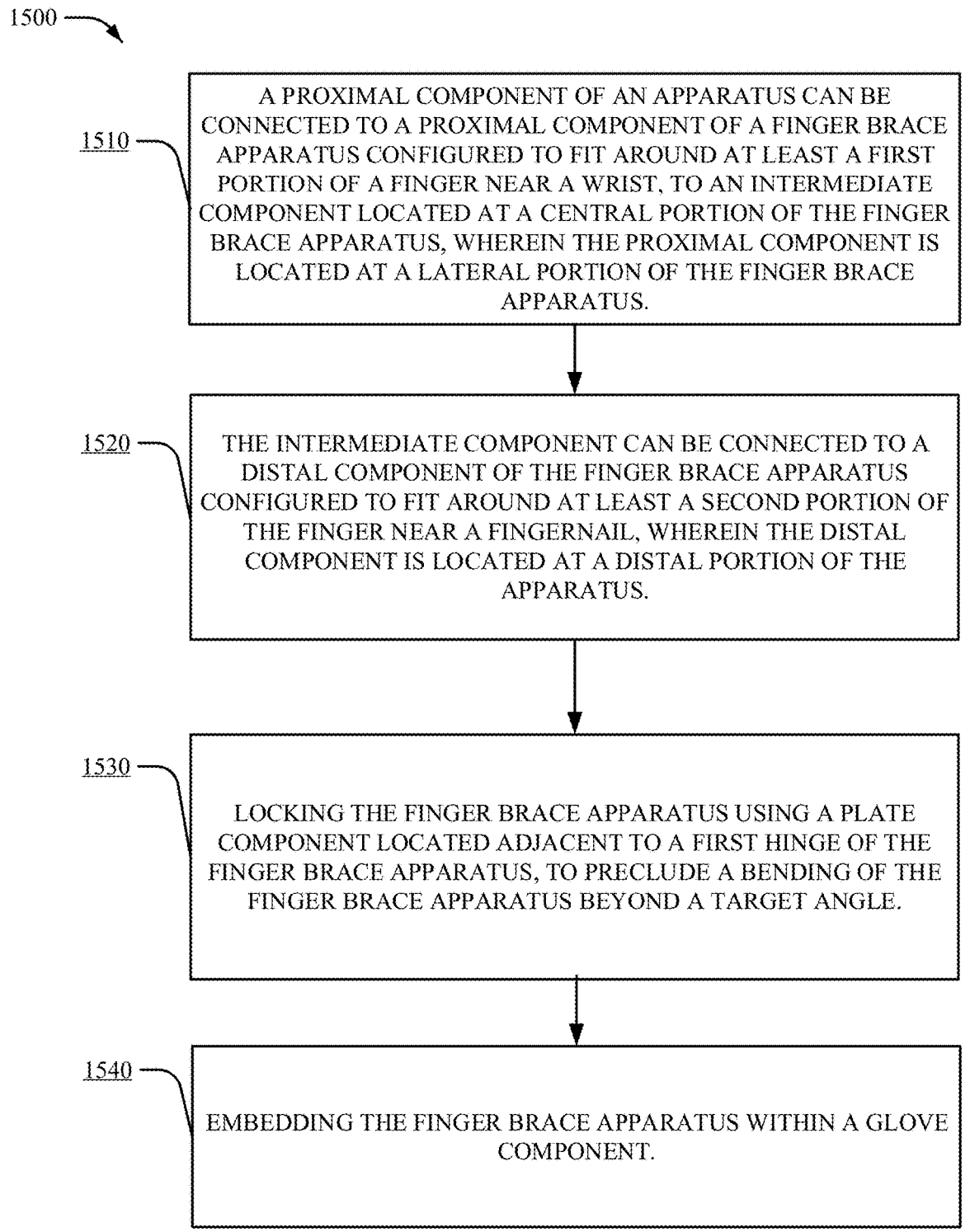
FIG. 15 illustrates a flow diagram of an example, non-limiting assembly method that facilitates an assembly of a finger brace apparatus in accordance with one or more embodiments described herein.

FIG. 15 illustrates a flow diagram of an example, non-limiting assembly method 1500 that facilitates an assembly of a finger brace apparatus in accordance with one or more embodiments described herein. Repetitive description of like elements employed in other embodiments described herein is omitted for sake of brevity. In some implementations, at reference numeral 1502, a proximal component of an apparatus (e.g., apparatus 10) can be connected to a proximal component of a finger brace apparatus, configured to fit around at least a first portion of a finger near a wrist, to an intermediate component located at a central portion of the finger brace apparatus, wherein the proximal component is located at a lateral portion of the finger brace apparatus.

At 1504, the intermediate component can be connected to a distal component of the finger brace apparatus configured to fit around at least a second portion of the finger near a fingernail, wherein the distal component is located at a distal portion of the apparatus. At 1506, the finger brace apparatus can be locked, using a plate component 24 located adjacent to a first hinge of the finger brace apparatus, to preclude a bending of the finger brace apparatus beyond a target angle. At 1508, the finger brace apparatus can be embedded within a glove component.

It will be appreciated that the finger brace apparatus described herein are illustrative and that variations and modifications are possible. For instance, the apparatuses may employ one or more adaptations to increase comfort and/or effectiveness. For example, the apparatuses may have portions comprising a gel, a viscoelastic material, cushioning, foam or other variations in materials. In addition, one or more glove coverings may be employed on all or portions of the apparatus such as nylon, cotton, silk or felt.

In the description, various embodiments have been described. For purposes of explanation, specific configurations and details are set forth in order to provide a thorough understanding of the embodiments. It will also be apparent to one skilled in the art that the present invention can be practiced without the specific details described herein. Furthermore, well-known features may be omitted or simplified in order not to obscure the embodiment being described.

Certain embodiments of the present invention relate to hinge finger brace apparatuses. In another embodiment, the finger brace may employ one or more sensors to retrieve data associated with use of the finger guard 10 and/or any of the embodiments disclosed herein. In an aspect, finger guard 10 can include a processor that can execute components and/or computer instructions. Furthermore, finger guard 10 can include a memory that can store computer executable components and/or instructions. In an aspect, finger guard 10 can retrieve data associated with the use of finger guard 10. In another aspect, the received data can represent metrics associated with finger movements to evaluate motor functions of a hand and fingers. In an aspect, finger movement data can be retrieved from sensors such as accelerometers, dynamometer, piezoelectric buttons, signal to noise ration detecting devices, load cells, optical switches, and other such electronics that can be integrated into the finger guard 10 (and/or finger guard 30) and/or a glove that is capable of integrating a finger guard 10. Other data representations include compression force measurements, pressure change metrics, force exerted by a finger metric, base line data, rest data, and other such finger and hand use data.

In an aspect, one or more sensor can include a bending sensor that receive sensory data from use or activity of the finger brace apparatus. For instance, a rotation sensor can detect data associated with positions of a finger brace user wrist at various times during gameplay or activities performed during use of the apparatus. Furthermore, motion sensors and/or pressure sensors/force sensors can be mounted to the apparatus to receive data associated with pressures exerted on any given finger and wrist while using the brace.

Furthermore, the data can include time period data representing a period of time in which pressure is applied to fingers, thumbs, and wrists protected by the brace (e.g., continuous pressure is applied to particular areas of the hand, intermittent pressure is applied, uniform vs uneven pressure being applied to areas of the hand, identify target pressure sites/localized areas of pressure receiving various forces of pressure and potentially limiting a vascular flow path throughout the hand or fingers, etc.). The sensors can be embedded within or mounted upon the finger brace apparatus, within the glove or within any padding associated with the glove and/or finger brace apparatus. In yet another aspect, the motion sensor can receive data representing sensed movement (e.g., velocity of finger motion measurements, range of motion of each finger digit, etc.) and positions of the fingers or hand while using the finger brace apparatus.

In another aspect, a sensor component can be embedded in a glove or finger cover that fits over a finger brace apparatus. The glove can utilize infrared light to measure changes in the amount of light received by a sensor fixed across from the infrared light source. Accordingly, the sensor can record metrics such as blood density, heartbeat, and other heart health metrics using the infrared light source mechanism. In another aspect, one or more pulse oximetry sensor can be mounted to the finger brace apparatus (any of the several embodiments).

While the present invention can be useful to produce finger braces for a wide variety of uses, some embodiments of the invention are may be used for producing finger braces for applications such as construction activities, athletic activities (e.g., football, basketball, etc.). In the foregoing specification, embodiments of the invention have been described with reference to numerous specific details that may vary from implementation to implementation. The specification and drawings are, accordingly, to be regarded in an illustrative rather than a restrictive sense.

Figure 16:
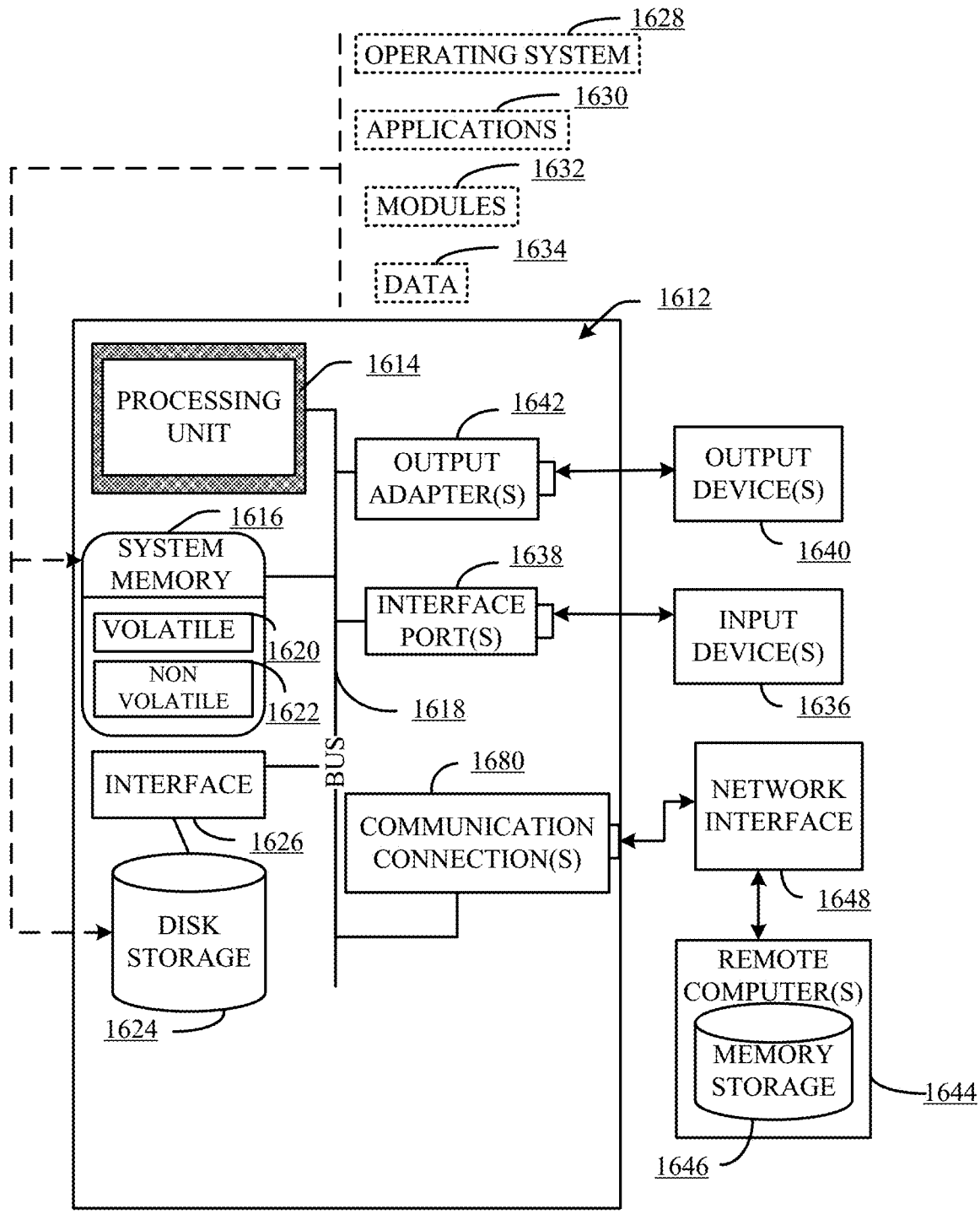
FIG. 16 illustrates a block diagram of an example, non-limiting operating environment in which one or more embodiments described herein can be facilitated.

In order to provide a context for the various aspects of the disclosed subject matter, FIG. 16 as well as the following discussion is intended to provide a general description of a suitable environment in which the various aspects of the disclosed subject matter can be implemented. FIG. 16 illustrates a block diagram of an example, non-limiting operating environment in which one or more embodiments described herein can be facilitated. With reference to FIG. 16, a suitable operating environment 1600 for implementing various aspects of this disclosure can also include a computer 1612. The computer 1612 can also include a processing unit 1614, a system memory 1616, and a system bus 1618. The system bus 1618 couples system components including, but not limited to, the system memory 1616 to the processing unit 1614. The processing unit 1614 can be any of various available processors. Dual microprocessors and other multiprocessor architectures also can be employed as the processing unit 1614. The system bus 1618 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire (IEEE 1394), and Small Computer Systems Interface (SCSI).

The system memory 1616 can also include volatile memory 1620 and nonvolatile memory 1622. The basic input/output system (BIOS), containing the basic routines to transfer information between elements within the computer 1612, such as during start-up, is stored in nonvolatile memory 1622. By way of illustration, and not limitation, nonvolatile memory 1622 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 1620 can also include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 1612 can also include removable/non-removable, volatile/nonvolatile computer storage media. FIG. 16 illustrates, for example, a disk storage 1624. Disk storage 1624 can also include, but is not limited to, devices like a magnetic disk drive, floppy disk drive, tape drive, Jaz drive, Zip drive, LS-100 drive, flash memory card, or memory stick. The disk storage 1624 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1624 to the system bus 1618, a removable or non-removable interface is typically used, such as interface 1626. FIG. 16 also depicts software that acts as an intermediary between users and the basic computer resources described in the suitable operating environment 1600. Such software can also include, for example, an operating system 1628. Operating system 1628, which can be stored on disk storage 1624, acts to control and allocate resources of the computer 1612.

System applications 1630 take advantage of the management of resources by operating system 1628 through program modules 1632 and program data 1634, e.g., stored either in system memory 1616 or on disk storage 1624. It is to be appreciated that this disclosure can be implemented with various operating systems or combinations of operating systems. A user enters commands or information into the computer 1612 through input device(s) 1636. Input devices 1636 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1614 through the system bus 1618 via interface port(s) 1638. Interface port(s) 1638 include, for example, a serial port, a parallel port, a game port, and a universal serial bus (USB). Output device(s) 1640 use some of the same type of ports as input device(s) 1636. Thus, for example, a USB port can be used to provide input to computer 1612, and to output information from computer 1612 to an output device 1640. Output adapter 1642 is provided to illustrate that there are some output device 1640 like monitors, speakers, and printers, among other such output device 1640, which require special adapters. The output adapters 1642 include, by way of illustration and not limitation, video and sound cards that provide a means of connection between the output device 1640 and the system bus 1618. It should be noted that other devices and/or systems of devices provide both input and output capabilities such as remote computer(s) 1644.

Computer 1612 can operate in a networked environment using logical connections to one or more remote computers, such as remote computer(s) 1644. The remote computer(s) 1644 can be a computer, a server, a router, a network PC, a workstation, a microprocessor based appliance, a peer device or other common network node and the like, and typically can also include many or all of the elements described relative to computer 1612. For purposes of brevity, only a memory storage device 1646 is illustrated with remote computer(s) 1644. Remote computer(s) 1644 is logically connected to computer 1612 through a network interface 1648 and then physically connected via communication connection 1650. Network interface 1648 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1650 refers to the hardware/software employed to connect the network interface 1648 to the system bus 1618. While communication connection 1650 is shown for illustrative clarity inside computer 1612, it can also be external to computer 1612. The hardware/software for connection to the network interface 1648 can also include, for exemplary purposes only, internal and external technologies such as, modems including regular telephone grade modems, cable modems and DSL modems, ISDN adapters, and Ethernet cards.

Figure 17:
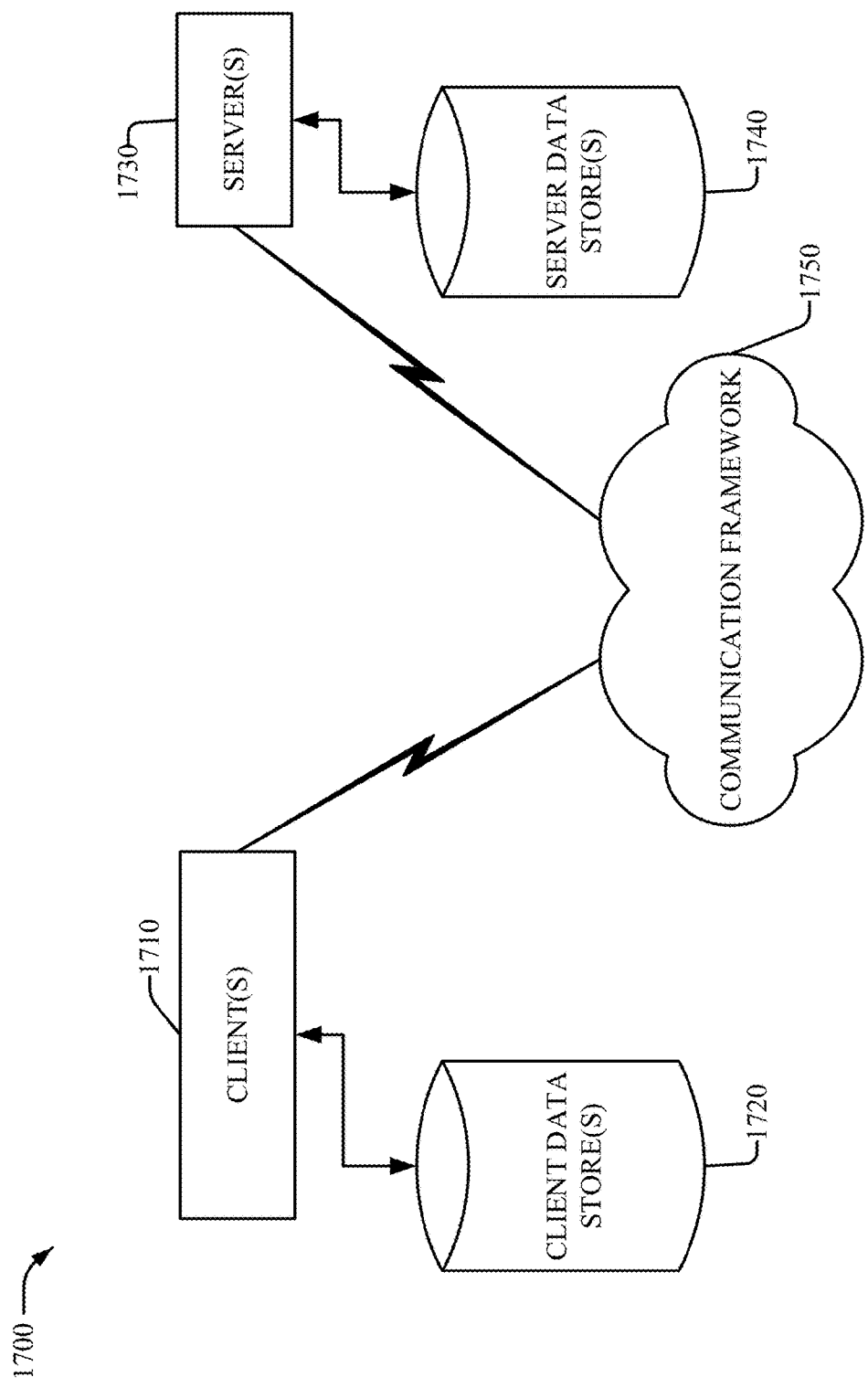
FIG. 17 illustrates a block diagram representing an exemplary non-limiting computing system or operating environment in which the various embodiments may be implemented.

Referring now to FIG. 17, there is illustrated a schematic block diagram of a computing environment 1700 in accordance with this disclosure. The system 1700 includes one or more client(s) 1702 (e.g., laptops, smart phones, PDAs, media players, computers, portable electronic devices, tablets, and the like). The client(s) 1702 can be hardware and/or software (e.g., threads, processes, computing devices). The system 1700 also includes one or more server(s) 1704. The server(s) 1704 can also be hardware or hardware in combination with software (e.g., threads, processes, computing devices). The servers 1704 can house threads to perform transformations by employing aspects of this disclosure, for example. One possible communication between a client 1702 and a server 1704 can be in the form of a data packet transmitted between two or more computer processes wherein the data packet may include video data. The data packet can include a metadata, e.g., associated contextual information, for example. The system 1700 includes a communication framework 1706 (e.g., a global communication network such as the Internet, or mobile network(s)) that can be employed to facilitate communications between the client(s) 1702 and the server(s) 1704.

Communications can be facilitated via a wired (including optical fiber) and/or wireless technology. The client(s) 1702 include or are operatively connected to one or more client data store(s) 1708 that can be employed to store information local to the client(s) 1702 (e.g., associated contextual information). Similarly, the server(s) 1204 are operatively include or are operatively connected to one or more server data store(s) 1710 that can be employed to store information local to the servers 1704. In one embodiment, a client 1702 can transfer an encoded file, in accordance with the disclosed subject matter, to server 1704. Server 1704 can store the file, decode the file, or transmit the file to another client 1702. It is to be appreciated, that a client 1702 can also transfer uncompressed file to a server 1704 and server 1704 can compress the file in accordance with the disclosed subject matter. Likewise, server 1704 can encode video information and transmit the information via communication framework 1706 to one or more clients 1702.

The present disclosure may be a system, a method, an apparatus and/or a computer program product at any possible technical detail level of integration. The computer program product can include a computer readable storage medium (or media) having computer readable program instructions thereon for causing a processor to carry out aspects of the present disclosure. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of the present disclosure can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or non-volatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. An apparatus comprising:
    a ball joint proximal component connected to an intermediate component via a first hinge component,
    wherein a peg receiving portion extends from an end portion of the ball joint proximal component, and wherein a rod portion connected to a ball portion protrudes from another end portion of the ball joint proximal component;
    a distal component connected to the intermediate component via a second hinge component,
    a hand plate component comprising five socket portions;
    wherein five ball portions of five ball joint proximal components are configured to integrate with the five socket portions of the hand plate component configured to sit on a back portion of a user hand and allow for a three sixty degree pivoting motion of the five ball portions within the five socket portions respectively,
    wherein the hand plate component is configured as a stable anchor for the ball joint proximal component,
    wherein the five ball portions interlocked with the five socket portions are configured to inhibit a flexion of a user finger beyond a hyperextension range of motion,
    wherein the peg receiving portion is a first pivot element of the first hinge component,
    wherein a rounded semicircle outer edge of the peg receiving portion circumscribes a first peg protruding from the intermediate component,
        wherein the first peg is a second pivot element of the first hinge component,
        wherein a three-sided plate component protrudes from a side portion of the intermediate component,
        wherein the intermediate component comprises a first dome-shaped top portion configured to connect first side portions of the intermediate component,
        wherein the first dome-shaped top portion comprises a first outer edge wall,
        wherein the distal component comprises a second dome-shaped top portion configured to connect second side portions of the distal component,
        wherein the second dome-shaped top portion comprises a second outer edge wall
        wherein the first hinge component is a connection junction between the first peg of the intermediate component and the peg receiving portion of the ball joint proximal component,
    wherein the ball joint proximal component is configured to at least partially encase a bottom segment of the user finger, wherein the intermediate component is configured to at least partially encase a middle segment of the user finger,
    wherein the first hinge component is configured to:
        restrict a first bending motion beyond a first defined degree of bend based on an impact between the three-sided plate component and the rounded semicircle outer edge, wherein the first bending motion conforms to a first joint movement between the bottom segment and the middle segment of the user finger; and
    wherein the second hinge component is another connection junction between a second peg of the distal component and another peg receiving portion of the intermediate component,
    wherein the distal component is configured to at least partially encase a tip segment of the user finger, and
    wherein the second hinge is configured to:
        restrict a second bending motion beyond a second defined degree of bend based on an impact between the first outer edge wall and the second outer edge wall, wherein the second bending motion conforms to a second joint movement between the tip segment of the user finger and the middle segment of the user finger.

2. The apparatus of claim 1, wherein the first dome-shaped top portion comprises a first curvature that transitions into the first side portions of the intermediate component that are less curved than the first curvature, wherein the first dome-shaped top portion is configured to encase a top portion of the middle segment of the finger, wherein the first side walls are configured to encase side portions of the middle segment of the finger, and wherein a first temperature regulating opening is located between the first dome-shaped top portion and the second dome-shaped top portion.

3. The apparatus of claim 2, wherein the second dome-shaped top portion comprises a second curvature that transitions into the second side portions of the distal component that are less curved than the second curvature, wherein the second dome-shaped top portion is configured to encase a top portion of the distal segment of the finger, wherein a second temperature regulating opening is located between the first dome-shaped top portion and a third dome shaped top portion comprising a third curvature that transitions into third side portions of the ball joint proximal component that are less curved than the third curvature.

4. The apparatus of claim 3, wherein the second temperature regulating opening is larger than the first temperature regulating opening.

5. The apparatus of claim 1, wherein the three-sided plate comprises a first edge, a second edge, and a third edge, wherein the first edge of the three-sided plate is configured to lodge against the first hinge at a first maximum degree of bending between the ball joint proximal component and the intermediate component, wherein the first edge is perpendicular to the second edge, and wherein the first edge is shorter in length than the second edge.

6. The apparatus of claim 1, wherein a first position of the ball joint proximal component and a second position of the intermediate component corresponds to a first maximum degree of bending between the ball joint proximal component and the intermediate component via the first hinge.

7. The apparatus of claim 1, wherein a first length of the ball joint proximal component is greater than a second length of the intermediate component, and wherein the second length of the intermediate component is greater than a third length of the distal component.

8. The apparatus of claim 1, wherein the first hinge is configured to align with a first finger joint of a user finger, and wherein the second hinge is configured to align with a second finger joint of the user finger.

9. The apparatus of claim 1, wherein a first distal end and a second distal end of the ball joint proximal component are thicker or rounder than a first middle portion of the ball joint proximal component located between the first distal end and the second distal end, and wherein a third distal end and a fourth distal end of the intermediate component are thicker or rounder than a second middle portion of the intermediate component located between the third distal end and the fourth distal end.

10. The apparatus of claim 1, wherein the three-sided plate component is located adjacent to the first hinge component, wherein the three-sided plate component is a raised portion protruding from the side portion of the intermediate component, wherein the three-sided plate component is configured to lock the apparatus in a position based on a wedged interaction between the three-sided plate component and a rounded semicircle outer edge upon an occurrence of the first defined degree of bend between the proximal component and the intermediate component, and wherein the three-sided plate component comprises three sides that form three angles.

11. The apparatus of claim 10, wherein a locked position between the three-sided plate component and the first outer edge wall is configured to restrict the middle portion of a user finger from extending beyond the first defined degree of bend, wherein an extension beyond the first defined degree of bend represents a hyperextension of the user finger.

12. The apparatus of claim 11, wherein the predefined angle is ninety degrees.

13. The apparatus of claim 1, further comprising a connective band capable of binding two or more of the apparatus together, wherein the connective band is configured to fit to a set of user fingers respectively.

14. The apparatus of claim 1, further comprising a glove component configured to receive the apparatus.

15. The apparatus of claim 1, wherein the five ball portions integrated within the five socket portions is configured to enable a greater range of motion of the apparatus, as compared to a range of motion associated with a hinge connection between the proximal component and the hand plate component.

16. A method comprising:
providing an apparatus comprising:
a ball joint proximal component of a finger brace apparatus connected to an intermediate component of the finger brace apparatus via a first hinge component; wherein a peg receiving portion extends from an end portion of the ball joint proximal component, and wherein a rod portion connected to a ball portion protrudes from another end portion of the ball joint proximal component;
a distal component of the finger brace apparatus connected to the intermediate component via a second hinge component;
a hand plate component comprising five socket portions;
wherein five ball portions of five ball joint proximal components are configured to integrate with the five socket portions of the hand plate component configured to sit on a back portion of a user hand and allow for a three sixty degree pivoting motion of the five ball portions within the five socket portions respectively, wherein the hand plate component is configured as a stable anchor for the ball joint proximal component, wherein the five ball portions interlocked with the five socket portions are configured to inhibit a flexion of a user finger beyond a hyperextension range of motion;
connecting the ball joint proximal component to the intermediate component via the first hinge component; and
connecting the intermediate component to the distal component via the second hinge component;
wherein the peg receiving portion is a first pivot element of the first hinge component,
wherein a rounded semicircle outer edge of the peg receiving portion circumscribes a first peg protruding from the intermediate component,
wherein the first peg is a second pivot element of the first hinge component,
wherein a three-sided plate component protrudes from a side portion of the intermediate component,
wherein the intermediate component comprises a first dome-shaped top portion configured to connect first side portions of the intermediate component, wherein the first dome-shaped top portion comprises a first outer edge wall, wherein the distal component comprises a second dome-shaped top portion configured to connect second side portions of the distal component, wherein the second dome-shaped top portion comprises a second outer edge wall, wherein the first hinge component is a connection junction between the first peg of the intermediate component and the peg receiving portion of the ball joint proximal component, wherein the ball joint proximal component is configured to at least partially encase a bottom segment of a finger, wherein the intermediate component is configured to at least partially encase a middle segment of the users finger, wherein the first hinge component is configured to:
restrict a first bending motion beyond a first defined degree of bend based on an impact between the three-sided plate component and the rounded semicircle outer edge, wherein the first bending motion conforms to a first joint movement between the bottom segment and the middle segment of the users finger; and wherein the second hinge component is another connection junction between a second peg of the distal component and another peg receiving portion of the intermediate component, wherein the distal component is configured to at least partially encase a tip segment of the users finger, and wherein the second hinge is configured to:
restrict a second bending motion beyond a second defined degree of bend based on an impact between the first outer edge wall and the second outer edge wall, wherein the second bending motion conforms to a second joint movement between the tip segment of the users finger and the middle segment of the users finger.

17. The method of claim 16, further comprising locking, using the three-sided plate component located adjacent to the first hinge component of the finger brace apparatus, the intermediate component and the proximal component in place to preclude a bending of the finger brace apparatus beyond a target angle.

18. The method of claim 16, further comprising connecting the finger brace apparatus with another finger brace apparatus via a band.

19. The method of claim 16, further comprising embedding the finger brace apparatus within a glove component.

20. A method comprising:
providing an apparatus comprising:
a ball joint proximal component of a finger brace apparatus connected to an intermediate component of the finger brace apparatus via a first hinge component; wherein a peg receiving portion extends from an end portion of the ball joint proximal component, and wherein a rod portion connected to a ball portion protrudes from another end portion of the ball joint proximal component;
a distal component of the finger brace apparatus connected to the intermediate component via a second hinge component;
a hand plate component comprising five socket portions;
wherein five ball portions of five ball joint proximal components are configured to integrate with the five socket portions of the hand plate component configured to sit on a back portion of a user hand and allow for a three sixty degree pivoting motion of the five ball portions within the five socket portions respectively, wherein the hand plate component is configured as a stable anchor for the ball joint proximal component, wherein the five ball portions interlocked with the five socket portions are configured to inhibit a flexion of a user finger beyond a hyperextension range of motion;

connecting the ball joint proximal component of the finger brace apparatus to the intermediate component of the finger brace apparatus using the first hinge component comprising a first pair of revolute joint hinges; and connecting the intermediate component to the distal component of the finger brace apparatus using the second hinge component that is a second pair of revolute joint hinges; and affixing a three-sided plate component to a first outer edge wall of the intermediate component and adjacent to a first revolute joint hinge of the first pair of revolute joint hinges;
wherein the peg receiving portion is a first pivot element of the first hinge component,
wherein a rounded semicircle outer edge of the peg receiving portion circumscribes a first peg protruding from the intermediate component,
wherein the first peg is a second pivot element of the first hinge component,
wherein a three-sided plate component protrudes from a side portion of the intermediate component,
wherein the intermediate component comprises a first dome-shaped top portion configured to connect first side portions of the intermediate component,
wherein the first dome-shaped top portion comprises a first outer edge wall,
wherein the distal component comprises a second dome-shaped top portion configured to connect second side portions of the distal component,
wherein the second dome-shaped top portion comprises a second outer edge wall,
wherein the first hinge component is a connection junction between the first peg of the intermediate component and the peg receiving portion of the ball joint proximal component,
wherein the ball joint proximal component is configured to at least partially encase a bottom segment of a finger, wherein the intermediate component is configured to at least partially encase a middle segment of the users finger,
wherein the first hinge component is configured to:
restrict a first bending motion beyond a first defined degree of bend based on an impact between the three-sided plate component and the rounded semicircle outer edge, wherein the first bending motion conforms to a first joint movement between the bottom segment and the middle segment of the users finger; and
wherein the second hinge component is another connection junction between a second peg of the distal component and another peg receiving portion of the intermediate component,
wherein the distal component is configured to at least partially encase a tip segment of the users finger, and
wherein the second hinge is configured to:
restrict a second bending motion beyond a second defined degree of bend based on an impact between the first outer edge wall and the second outer edge wall, wherein the second bending motion conforms to a second joint movement between the tip segment of the users finger and the middle segment of the users finger.

* * * * *